(12) United States Patent
Lynn et al.

(10) Patent No.: US 7,883,720 B2
(45) Date of Patent: Feb. 8, 2011

(54) CHARGE-DYNAMIC POLYMERS AND DELIVERY OF ANIONIC COMPOUNDS

(75) Inventors: David M. Lynn, Middleton, WI (US); Adam D. Miller, Berkeley, CA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 596 days.

(21) Appl. No.: 10/886,161

(22) Filed: Jul. 7, 2004

(65) Prior Publication Data
US 2005/0027064 A1 Feb. 3, 2005

Related U.S. Application Data

(60) Provisional application No. 60/486,107, filed on Jul. 9, 2003.

(51) Int. Cl.
 A61K 9/00 (2006.01)
 C12N 15/00 (2006.01)
 C08F 283/06 (2006.01)
 A61K 47/00 (2006.01)

(52) U.S. Cl. ............... 424/450; 424/280.1; 424/452; 424/486; 424/487; 424/489; 424/499; 435/6; 435/69.1; 435/455; 435/458; 435/459; 435/463; 435/465; 514/44; 514/54; 514/772.1; 514/772.2; 514/772.3

(58) Field of Classification Search ........... 525/54.1, 525/54.11, 54.2; 424/78.27, 450, 452, 489, 424/486, 487, 280.1, 499; 522/1, 150; 435/6, 435/69.1, 455, 458, 459, 463, 465; 514/44, 514/54, 772.1, 772.2, 772.3
See application file for complete search history.

(56) References Cited

U.S. PATENT DOCUMENTS

| | | | |
|---|---|---|---|
| 4,304,705 A | 12/1981 | Heilmann et al. |
| 4,451,619 A | 5/1984 | Heilmann et al. |
| 4,485,236 A | 11/1984 | Rasmussen et al. |
| 4,639,286 A | 1/1987 | Rasmussen et al. |
| 4,871,824 A | 10/1989 | Heilmann et al. |
| 4,981,933 A | 1/1991 | Fazio et al. |
| 5,013,795 A | 5/1991 | Coleman et al. |
| 5,039,813 A | 8/1991 | Fazio et al. |
| 5,081,197 A | 1/1992 | Heilmann et al. |
| 5,091,489 A | 2/1992 | Heilmann et al. |
| 5,149,806 A | 9/1992 | Moren et al. |
| 5,262,484 A | 11/1993 | Coleman et al. |
| 5,266,446 A | 11/1993 | Chang et al. |
| 5,336,742 A | 8/1994 | Heilmann et al. |
| 5,419,806 A | 5/1995 | Huebner et al. |
| 5,486,358 A | 1/1996 | Coleman et al. |
| 5,567,422 A | 10/1996 | Greenwald |
| 5,741,620 A | 4/1998 | Holmes et al. |
| 5,837,751 A | 11/1998 | Jacobine et al. |
| 5,948,878 A | 9/1999 | Burgess et al. |
| 6,217,912 B1 | 4/2001 | Park et al. |
| 6,245,922 B1 | 6/2001 | Heilmann et al. |
| 6,274,322 B1 | 8/2001 | Curiel et al. |
| 6,291,216 B1 | 9/2001 | Muller et al. |
| 6,312,727 B1 | 11/2001 | Schacht et al. |
| 6,353,055 B1 | 3/2002 | Kabanov et al. |
| 6,365,173 B1 | 4/2002 | Domb et al. |
| 6,379,952 B1 | 4/2002 | Rasmussen et al. |
| 6,383,811 B2 | 5/2002 | Wolff et al. |
| 6,395,253 B2 | 5/2002 | Levy et al. |
| 6,544,790 B1 | 4/2003 | Sabatini |
| 6,586,524 B2 | 7/2003 | Sagara |
| 6,652,886 B2 | 11/2003 | Ahn et al. |
| 6,740,643 B2 | 5/2004 | Wolff et al. |
| 6,743,521 B2 | 6/2004 | Hubbell et al. |
| 6,770,740 B1 | 8/2004 | Rice et al. |
| 6,998,115 B2 | 2/2006 | Langer et al. |
| 7,112,361 B2 | 9/2006 | Lynn et al. |
| 7,332,546 B2 | 2/2008 | Fansler et al. |
| 7,368,296 B2 | 5/2008 | Edwards et al. |
| 2001/0006817 A1 | 7/2001 | Pack et al. |
| 2001/0025015 A1 | 9/2001 | Volker et al. |
| 2001/0031839 A1 | 10/2001 | Muller et al. |
| 2002/0012652 A1 | 1/2002 | Levy et al. |
| 2002/0131951 A1 | 9/2002 | Langer et al. |
| 2002/0146459 A1 | 10/2002 | Levy et al. |
| 2002/0150951 A1 | 10/2002 | Rasmussen et al. |

(Continued)

FOREIGN PATENT DOCUMENTS

WO    WO 03/035716    5/2003

(Continued)

OTHER PUBLICATIONS

International Search Report issued May 12, 2005 for PCT/US04/21787.

(Continued)

*Primary Examiner*—Ana L Woodward
(74) *Attorney, Agent, or Firm*—Greenlee Sullivan PC

(57) ABSTRACT

The present invention provides dynamic charge state cationic polymers that are useful for delivery of anionic molecules. The dynamic charge state cationic polymers are designed to have cationic charge densities that decrease by removal of removable functional groups from the polymers. The present invention also provides interpolyelectrolyte complexes containing the polymers complexed to a polyanion. Methods for using the interpolyelectrolyte complexes to deliver anionic compounds are also provided.

33 Claims, 11 Drawing Sheets

U.S. PATENT DOCUMENTS

| | | |
|---|---|---|
| 2002/0164315 A1 | 11/2002 | Wolff et al. |
| 2003/0026840 A1 | 2/2003 | Plank et al. |
| 2003/0049435 A1 | 3/2003 | Haddah et al. |
| 2003/0073619 A1 | 4/2003 | Mahato et al. |
| 2005/0027064 A1* | 2/2005 | Lynn et al. .................. 524/555 |
| 2005/0265956 A1* | 12/2005 | Liu et al. .................. 424/78.27 |
| 2005/0282925 A1 | 12/2005 | Schlenoff et al. |
| 2006/0051396 A1 | 3/2006 | Hamilton et al. |
| 2006/0068204 A1 | 3/2006 | Rasmussen et al. |
| 2006/0093607 A1 | 5/2006 | Gerber et al. |
| 2006/0251701 A1 | 11/2006 | Lynn et al. |
| 2007/0020469 A1 | 1/2007 | Wood et al. |

FOREIGN PATENT DOCUMENTS

| | | |
|---|---|---|
| WO | WO 2004/009665 | 1/2004 |
| WO | WO 2004/009666 | 1/2004 |
| WO | WO 2004/106411 | 12/2004 |
| WO | WO 2005/007819 | 1/2005 |
| WO | WO 2007/140391 | 12/2007 |
| WO | WO 2007/140402 | 12/2007 |
| WO | WO 2009/049092 | 4/2009 |
| WO | WO 2009/049100 | 4/2009 |

OTHER PUBLICATIONS

Funhoff, A. M. et al., "Polymer Side-Chain Degradation as a Tool to Control the Destabilization of Polyplexes," *Pharmaceutical Research*, vol. 21, No. 1, pp. 170-176, Jan. 2004; published by Plenum Publishing Corporation.

Godbey, W. T. et al., "Tracking the intracellular path of poly(ethylenimine)/DNA complexes for gene delivery," *Proc. Natl. Acad. Sci. USA*. vol. 96. pp. 5177-5181. Apr. 1999.

Jeong, J. H. et al., "DNA transfection using linear poly(ethylenimine) prepared by controlled acid hydrolysis of poly(2-ethyl-2-oxazoline)," *Jounral of Controlled Release*, vol. 73, pp. 391-399, 2001; published by Elsevier Science B.V.

Zelilkin, A. N. et al., "Competitive Reactions in Solutions of Poly-L-histidine, Calf Thymus DNA, and Synthetic Polyanions: Determining the Binding Constants of Polyelectrolytes," *J. Am. Chem. Soc.*, vol. 125, pp. 13693-13699, 2003; published by American Chemical Society.

Kircheis, R. et al., "Design and gene delivery activity of modified polyethylenimines," *Advanced Drug Delivery Reviews*, vol. 53, pp. 341-358, 2001; published by Elsevier Science B.V.

Bronich, T. K. et al., "Recognition of DNA Topology in Reactions between Plasmid DNA and Cationic Copolymers," *J. Am. Chem. Soc.*, vol. 122, No. 35, pp. 8339-8343, Sep. 6, 2000; published by American Chemical Society.

Prata, C. A. H. et al., "Charge-Reversal Amphiphiles for Gene Delivery," *J. Am. Chem. Soc.*, received Apr. 20, 2004.

Lynn, D. M. et al., "Degradable Poly(β-amino esters): Synthesis, Characterization, and Self-Assembly with Plasmid DNA," *J. Am. Chem. Soc.*, vol. 122, pp. 10761-10768, 2000; published by American Chemical Society.

Schaffer, D. V. et al., "Vector Unpacking as a Potential Barrier for Receptor-Mediated Polyplex Gene Delivery," *Biotechnology and Bioengineering*, vol. 67, No. 5, pp. 598-606, 2000; published by John Wiley & Sons, Inc.

Pichon, C. et al., "Poly[Lys-(AEDPT)]: A Cationic Polymer That Allows Dissociation of pDNA/Cationic Polymer Complexes in a Reductive Medium and Enhances Polyfection," *Bioconjugate Chem.*, vol. 13, pp. 76-82, 2002; published by American Chemical Society.

Lynn, D. M. et al., "Accelerated Discovery of Synthetic Transfection Vectors: Parallel Synthesis and Screening of a Degradable Polymer Library," *J. Am. Chem. Soc.*, vol. 123, pp. 8155-8156, 2001; published by American Chemical Society.

Forrest, M. L. et al., "Partial Acetylation of Polyethylenimine Enhances in Vitro Gene Delivery," *Pharmaceutical Research*, vol. 21, No. 2, pp. 365-371, Feb. 2004; published by Plenum Publishing Corporation.

Wang, J. et al., "A Novel Biodegradable Gene Carrier Based on Polyphosphoester," *J. Am. Chem. Soc.*, vol. 123, pp. 9480-9481, 2001; published by American Chemical Society.

Yin, R. et al., "Architectural Copolymers: Rod-Shaped, Cylindrical Dendrimers," *J. Am. Chem. Soc.*, vol. 120, pp. 2678-2679, 1998; published by American Chemical Society.

Lim, Y.-beom at al., "Development of a Safe Gene Delivery System Using Biodegradable Polymer, Poly[α-(4-aminobutyl)-L-glycolic acid]," *J. Am. Chem. Soc.*, vol. 122, pp. 6524-6525, 2000; published by American Chemical Society.

Suh, J. et al., "Efficient active transport of gene nanocarriers to the cell nucleus," *PNAS*, vol. 100, No. 7, pp. 3878-3882, Apr. 1, 2003.

Gosselin, M. A. et al., "Efficient Gene Transfer Using Reversibly Cross-Linked Low Molecular Weight Polyethylenimine," *Bioconjugate Chem.*, vol. 12, pp. 989-994, 2001; published by American Chemical Society.

Oupicky, D. at al., "Laterally Stabilized Complexes of DNA with Linear Reducible Polycations: Strategy for Triggered Intracellular Activation of DNA Delivery Vectors," *J. Am. Chem. Soc.*, vol. 124, No. 1, pp. 8-9, 2002; published by American Chemical Society.

Thomas, M. et al., "Enhancing polyethylenimine's delivery of plasmid DNA into mammalian cells," *PNAS*, vol. 99, No. 23, pp. 14640-14645, Nov. 12, 2002.

Akinc, A. et al., "Parallel Synthesis and Biophysical Characterization of a Degradable Polymer Library for Gene Delivery," *J. Am. Chem. Soc.*, received Jan. 30, 2003.

Vázquez, E. et al., "Construction of Hydrolytically-Degradable Thin Films via Layer-by-Layer Deposition of Degradable Polyelectrolytes," *J. Am. Chem. Soc.*, vol. 124, pp. 13992-13993, 2002; published by American Chemical Society.

Luo, D. et al., "Synthetic DNA delivery systems," *Nature Biotechnology*, vol. 18, pp. 33-37, Jan. 2000: published by Nature America Inc.

Putnam, D. et al., "Polymer-based gene delivery with low cytotoxicity by a unique balance of side-chain termini," *PNAS*, vol. 98, No. 3, pp. 1200-1205, Jan. 30, 2001.

Boussif, O. et al., "A versatile vector for gene and oligonucleotide transfer into cells in culture and in vivo: Polyethylenimine," *Proc. Natl. Acad. Sci. USA*, vol. 92, pp. 7297-7301, Aug. 1995.

Anderson, W. F., "Human Gene Therapy." *Nature*, vol. 392, Supp., Apr. 30, 1998, pp. 25-30; published by Macmillan Publishers Ltd. (London, England).

Verma, I. M. et al., "Gene Therapy—Promises, Problems and Prospects," *Nature*, vol. 389, Sep. 18, 1997, pp. 239-242; published by Macmillan Publishers Ltd. (London, England).

Crystal, R. G., "Transfer of Genes to Humans: Early Lessons and Obstacles to Success," *Science*, New Series, vol. 270, No. 5235, Oct. 20, 1995, pp. 404-410; published by American Association for the Advancement of Science (Washington, D.C.).

Midoux, P. et al., "Efficient Gene Transfer by Histidylated Polylysine/pDNA Complexes," *Bioconjugate Chem.*, vol. 10, 1999, pp. 406-411; published by American Chemical Society (Washington, D.C.).

Benns, J. M. et al., "pH-Sensitive Cationic Polymer Gene Delivery Vehicle: N-Ac-poly(L-histidine)-graft-poly(L-lysine) Comb Shaped Polymer," *Bioconjugate Chem.*, vol. 11, pp. 637-645, 2000; published by American Chemical Society (Washington, D.C.).

Wolff, J. A. et al., "Nuclear Security Breached," *Nature Biotechnology*, vol. 19, Dec. 2001, pp. 1118-1120; published by Nature Publishing Group (London, England).

Rebuffat, A. et al., "Selective Enhancement of Gene Transfer by Steroid-Mediated Gene Delivery," *Nature Biotechnology*, vol. 19, Dec. 2001, pp. 1155-1161; published by Nature Publishing Group (London.

Wolff, J. A., "'The Grand' Problem of Synthetic Delivery," *Nature Biotechnology*, vol. 20, Aug. 2002, pp. 768-769; published by Nature Publishing Group (London, England).

Petersen, H. et al., "Poly(ethylenimine-co-L-lactamide-co-succinamide): A Biodegradable Polyethylenimine Derivative with an Advantageous pH-Dependent Hydrolytic Degradation for Gene Delivery," *Bioconjugate Chem.*, vol. 13, pp. 812-821; published by American Chemical Society (Washington, D.C.).

Putnam, D. et al., "Poly(4-hydroxy-L-proline ester): Low-Temperature Polycondensation and Plasmid DNA Complexation," *Macro-

*molecules*, vol. 32, 1999, pp. 3658-3662; published by American Chemical Society (Washington, D.C.).

Godbey, W. T., "Size Matters: Molecular Weight Affects the Efficiency of Poly(ethylenimine) as a Gene Delivery Vehicle," *J. Biomed. Mater. Res.*, vol. 45, 1999, pp. 268-275; published by John Wiley & Sons, Inc.

Gonzalez, H. et al., "New Class of Polymers for the Delivery of Macromolecular Therapeutics," *Bioconjugate Chem.*, vol. 10, 1999, pp. 1068-1074; published by American Chemical Society (Washington, D.C.).

Fire, A. et al., "Potent and Specific Genetic Interference by Double-Stranded RNA in *Caenorhabditis elegans*," *Nature*, vol. 391, Feb. 19, 1998, pp. 806-811; published by Macmillan Publishers Ltd. (London, England).

Unkeless, J. C. et al., "Structure and Function of Human and Murine Receptors for IgG," *Ann. Rev. Immunol.*, vol. 6, 1988, pp. 251-281; published by Annual Reviews Inc.

Phillips, N. C. et al., "Enhanced Antibody Response to Liposome-Associated Protein Antigens: Preferential Stimulation of IgG2a/b Production," *Vaccine*, vol. 10, Issue 3, 1992, pp. 151-158; published by Butterworth-Heinemann Ltd (London, England).

Godbey, W. T. et al., "Tracking the Intracellular Path of Poly(ethylenimine)/DNA Complexes for Gene Delivery," *Proc. Natl. Acad. Sci. USA*, vol. 96, Apr. 1999, pp. 5177-5181; published by the National Academy of Science (Washington, D.C.).

Vogel, F. R. et al., A Compendium of Vaccine Adjuvants and Excipients ($2^{nd}$ Ed.), http://www.niaid.nih.gov/daids/vaccine/pdf/compendium.pdf.

Cotton, M. et al., "[42] Receptor-Mediated Transport of DNA into Eukaryotic Cells," *Methods in Enzymology*, vol. 217, 1993, pp. 618-644; published by Academic Press, Inc.

Allison, A. C., "The Mode of Action of Immunological Adjuvants," Modulation of the Immune Response to Vaccine Antigens, *Dev. Biol. Stand.* F. Brown and L. R. Haaheim (eds.), vol. 92, 1998, pp. 3-11.

Crooke, S. T., "Molecular Mechanisms of Action of Antisense Drugs," *Biochimica et Biophysica Acta*, vol. 1489, 1999, pp. 31-44; published by Elsevier Science B.V.

Crooke, S. T., "Evaluating the Mechanism of Action of Antiproliferative Antisense Drugs," *Antisense & Nucleic Acid Drug Development*, vol. 10, 2000, pp. 123-126; published by Mary Ann Liebert, Inc. (Larchmont, New York, USA).

Chan, P. P. et al., "Triplex DNA: Fundamentals, Advances, and Potential Applications for Gene Therapy," *J. Mol. Med.*, vol. 75, 1997, pp. 267-282; published by Springer-Verlag (Germany).

Mathiowitz, E. et al., "Polyanhydride Microspheres as Drug Carriers. II. Microencapsulation by Solvent Removal," *Journal of Applied Polymer Science*, vol. 35, 1988, pp. 755-774; published by John Wiley & Sons, Inc.

Mathiowitz, E. et al., "Novel Microcapsules for Delivery Systems," *Reactive Polymers*, vol. 6, 1987, pp. 275-283; published by Elsevier Science Publishers B.V. (Amsterdam—printed in the Netherlands).

Mathiowitz, E. et al., "Polyanhydride Microspheres as Drug Carriers—I. Hot-Melt Microencapsulation," *Journal of Controlled Release*, vol. 5, 1987, pp. 13-22; published by Elsevier Science Publishers B.V (Amsterdam—printed in the Netherlands).

Blacklock, J. et al. "disassembly of layer-by-layer films of plasmid DNA and reducible TAT polypeptide"; (2007) *Biomaterials* 28:117.

Chen, J. et al. "Tunable Film Degradation and Sustained Release of Plasmid DNA from Cleavable Polycation/Plasmid DNA Multilayers under Reductive Conditions"; (2007) *Small* 3:636.

Decher, G. "Fuzzy Nanoassemblies: Toward Layered Polymeric Multicomposites"; (1997) *Science* 277:1232.

De Geest, B.G. et al."Intracellularly Degradable Polyelectrolyte Microcapsules";(2006) *Adv. Mater.* 18:1005.

Fredin, N.J. et al. "Surface Analysis of Erodible Multilayered Polyelectrolyte Films: Nanometer-Scale Structure and Erosion Profiles"; (2005) *Langmuir* 21:5803.

Fredin, N.J. et al. "Nanometer-Scale Decomposition of Ultrathin Multilayered Polyelectrolyte Films"; (2007) *Langmuir* 23:2273.

Hammond, P.T. "Form and Function in Multilayer Assembly: New Applications at the Nanoscale"; (2004) *Adv. Mater.* 16:1271.

Heilmann, S.M. et al. "Highlight—Chemistry and Technology of 2-Alkenyl Azlactones"; (2001) *J. Polym. Sci. Poly. Chem.* 39:3655.

Jessel, N. et al. "Multiple and time-scheduled in situ DNA delivery mediated by β-cyclodextrin embedded in a polyelectrolyte multilayer"; (2006) *Proc. Natl. Acad. Sci. USA* 103:8618.

Jewell, C.M. et al."Release of Plasmid DNA from Intravascular Stents Coated with Ultrathin Multilayered Polyelectrolyte Films"; (2006) *Biomacromolecules* 7:2483.

Jewell, C.M. et al. "Multilayered polyelectrolyte films promote the direct and localized delivery of DNA cells"; (2005) *J.Control. Release* 106:214.

Klugherz, B.D. et al. "Gene delivery from a DNA controlled release stent in porcine coronary arteries"; (2000) *Nat. Biotechnol.* 18:1181.

Liu, X. et al. "Charge-Shifting Cationic Polymers that Promote Self-Assembly and Self-Disassembly with DNA"; (2005) *Macromolecules* 38:7907.

Luten, J. et al. "Methacrylamide Polymers with Hydrolysis-Sensitive Cationic Side Groups as Degradable Gene Carriers"; (2006) *Bioconjugate Chem.* 17:1077.

Lvov, Y. et al. "Assembly of Thin Films by Means of Successive Deposition of Alternate Layers of DNA and Poly(allylamine)";(1993) *Macromolecules* 26:5396.

Lynn, D.M. et al. "Layers of opportunity: nanostructured polymer assemblies for the delivery of macromolecular therapeutics"; (2006) *Soft Matter* 2:269.

Ren, K.F. et al. "Construction and enzymatic degradation of multilayered poly-L-lysine/DNA films"; (2006) *Biomaterials* 27:1152.

Ren, K.F. et al. "Tunable DNA Release from Cross-Linked Ultrathin DNA/PLL Multilayered Films"; (2006) *Bioconjugate Chem.* 17:77.

Segura, T. et al. Surf-tethered DNA Complexes for Enhanced Gene Delivery; (2002) *Bioconjugate Chem.* 13:621.

Shea, L.D. et al. "DNA delivery from polymer matrices for tissue engineering"; (1999) *Nat. Biotechnol.* 17:551.

Veron, L. et al. "New Hydrolyzable pH-Responsive Cationic Polymers for Gene Delivery: A Preliminary Study"; (2004) *Macromol. Biosci.* 4:431.

Wu, R.Z. et al. "Cell-biological applications of transfected-cell microarrays"; (2002) *Trends Cell Biol.* 12:485.

Zhang, J. et al. "Multilayered Thin Films that Sustain the Release of Functional DNA under Physiological Conditdions"; (2004) *Langmuir* 20:8015.

Ziauddin, J. et al. "Microarrays of cells expressing defined cDNAs"; (2001) *Nature* 411:107.

Barrera, et al. (1993) *J. Am. Chem. Soc.* 115:11010-11011.

Berg, C. et al. "Controlled Drug Release from Porous polyelectrolyte Multilayers"; (2006) *Biomacromolecules* 7:357-364.

Cotten et al. (1993) *Methods Enzymol* 217:618.

Fishbein, I. et al., "Site specific gene delivery in the cardiovascular system"; (2005) *J. Control Release* 109:37-48.

Fishbein, I. et al., "Bisphosphonate-mediated gene vector delivery from the metal surfaces of stents"; (2006) *Proc. Natl. Acad. Sci. USA* 103:159-164.

Goeddel, (1990) *Methods Enzymol* 185:3-7.

Groth, T. et al., "Layer-by-Layer Deposition of Polyelectrolytes—A Versatile tool for the In Vivo Repair of Blood Vessels"; (2004)*Agnew Chem. Int. Ed. Engl.*43:926-928.

Jewell et al., "Multilayered polyelectrolyte assemblies as platforms for the delivery of DNA and other nucleic acid-based therapeutics"; (2008) *Advanced Drug Delivery Reviews* 60:979-999.

Jewell et al., "Surface-mediated delivery of DNA: Cationic polymers take charge"; (2008) *Current Opinion in Colloid & Interface Science* 13:395-402.

Klugherz, B.D. et al., "Gene delivery from a DNA controlled-release stent in porcine coronary arteries"; (2000) *Nat. Biotechnol.* 18:1181-1184.

Kwon et al. (1989) *Macromolecules* 22:3250-3255.

Lim et al. (1999) *J. Am. Chem. Soc.* 121:5633-5639.

Lim, Y. et al. "Development of a Safe Gene Delivery System using Biodegradable Polymer, Poly[alpha-(4-aminobutyl)-L-glycolic acid]"; (2000) *J. Am. Chem. Soc.* 122:6524-6525.

Little, S.R. et al. "Poly-beta amino ester-containing microparticles enhance the activity of nonviral genetic vaccines"; (2004)*Proc. Natl. Acad. Sci. USA* 101:9534-9539.

Luo, D. et al., "Synthetic DNA delivery systems"; (2000) *Nat. Biotechnol.* 18:33-37.

Lynn, D.M. et al., "Degradable Poly(.beta.-Amino Esters): Synthesis, Characterization, and Self-Assembly with Plasmid DNA"; (2000) *J. Am. Chem. Soc.* 122:10761-10768.

Lynn et al., "Peeling Back the Layers: Controlled Erosion and Triggered Disassembly of Multilayered Polyelectrolyte Thin Films"; (2007) *Advanced Materials* 19:4118-4130.

Pack, D.W. et al. "Design and development of polymers for gene delivery"; (2005) *Nature Reviews Drug Discovery* 4:581-593.

Perlstein, I. et al., "DNA delivery from an intravascular stent with a denatured collagen-polylactic-polyglycolic acid-controlled release coating: mechanisms of enhanced transfection"; (2003) *Gene Therapy* 10:1420-1428.

Peterson, H. et al., "Poly(ethyleneimine-co-L-lactamide-co-succinamide): A Biodegradable Polyethyleneimine Derivative with an Advantageous pH-Dependent Hydrolytic Degradation for Gene Delivery"; (2002) *Bioconjugate Chem.* 13:812-821.

Peyratout, C.S. et al., "Tailor-made polyelectrolyte microcapsules: from multilayers to smart containers"; (2004) *Agnew Chem.Int. Ed. Engl.* 43:3762-3783.

Putnam, D. et al., "Poly(4-hydroxy-1-proline ester): Low-Temperature Polycondensation and Plasmid DNA Complexation"; (1999) *Macromolecules* 32:3658-3662.

Polycondensation and Plasmid DNA Complexation; (1999) *Macromolecules* 32:3658-3662.

Schuler, C. et al., "Decomposable hollow biopolymer-based capsules"; (2001) *Biomacromolecules* 2:921-926.

Sukhishvili, A., "Responsive polymer films and capsules via layer-by-layer assembly"; (2005) *Current Opinion in Colloid & Interface Science* 10:37-44.

Takahashi, A. et al., "Transgene delivery of plasmid DNA to smooth muscle cells and macrophages from a biostable polymer-coated stent" (2003) *Gene Therapy* 10:1471-1478.

Takahashi et al., "Delivery of Large Biopharmaceuticals from Cardiovascular Stents: A Review"; (2007) *Biomacromolecules*, 8(11):3281-3293.

Walter, D.H. et al., "Local gene transfer of phVEGF-2 plasmid by gene-eluting stents: an alternative strategy for inhibition of restenosis"; (2004) *Circulation* 110:36-45.

Wang, J. et al., "A Novel Biodegradable Gene Carrier Based on Polyphosphoester"; (2001) *J. Am. Chem. Soc.* 123:9480-9481.

Zhang, J. et al. "Erosion of Multilayered Films Fabricated from Degradable Polyamines: Characterization and Evidence in Support of a Mechanism that Involves Polymer Hydrolysis"; (2006) *J. of Polymer Science—Part A: Polymer Chemistry* 44: In Press.

Zhang, N.J. et al., "Structure/Property Relationships in Erodible Multilayered Films: Influence of Polycation Structure on Erosion profiles and the Release of Anionic Polyelectrolytes"; (2006) *Langmuir* 22:239-245.

Zhou et al (1990) *Macromolelcules* 23:3399-3406.

Ai et al. (Feb. 2003) "Biomedical Applications of Electrostatic Layer-by-Layer Nano-assembly of Polymers, Enzymes, and Nanoparticles," *Cell Biochem. Biophys.* 39(1):23-43.

Bertrand et al. (Apr. 2000) "Ultrathin Polymer Coatings by Complexation of Polyelectrolytes at Interfaces: Suitable Materials, Structure and Properties," *Macromol. Rapid Comm.* 21(7):319-348.

Bindels et al. (1985) *Biochem. Biophys. Acta.* 828:255-260.

Boulmedais et al. (2003) "Buildup of Exponentially Growing Multilayer Polypeptide Films with Internal Secondary Structure," *Langmuir* 19(2):440-445.

Chen et al. (2001) *Macromol. Rapid Commun.* 22:311-314.

Cho et al. (2003) "Polymeric Multilayer Films Comprising Deconstructable Hydrogen-Bonded Stacks Confined Between Electrostatically Assembled Layers," *Macromolecules* 36(8):2845-2851.

Donbrow, M. (1992) *Microcapsules and Nanoparticles in Medicine and Pharmacy*, CRC Press, Boca Raton.

Drtina et al. (1996) "Highly Cross-Linked Azlactone Functional Supports of Tailorable Polarity," *Macromolecules* 29(13):4486-4489.

Dubas et al. (2001) "Multiple Membranes from "True" Polyelectrolyte Multilayers," *J. Am. Chem. Soc.* 123(22):5368-5369.

Dubas et al. (2001) "Polyelectrlyte Multilayers Containing a Weak Polyacid: Construction and Deconstruction," *Macromolecules* 34(11):3736-3740.

Etienne et al. (2005) "Degradability of Polysaccharides Multilayer Films in the Oral Environment: An In Vitro and In Vivo Study," *Biomacromolecules* 6(2):726-733.

Feng et al. (2005) "Reactive Thin Films as Platforms for the Immobilization of Biomolecules," *Biomacromolecules* 6(6):3243-3251.

Grayson et al. (2003) "Multi-Pulse Drug Delivery from a Resorbable Polymeric Microchip Device," *Nat. Mater.* 2:767-772.

Guichard et al. (1998) *Macromol. Chem. Phys.* 199:1657-1674.

Hiller et al. (2002) "Reversibly Erasable Nanoporous Anti-Reflection Coatings from Polyelectrolyte Multilayers," *Nat. Mater.* 1:59-63.

International Search Report and Written Opinion Corresponding to International Application No. PCT/US08/79417, Mailed Dec. 22, 2008.

Jerome et al. (2003) "Preparation of Reactive Surfaces by Electrografting," *Chem. Commun.* 19:2500-2501.

Kirby et al. (1972) "Structure and Efficiency in Intramolecular and Enzymatic Catalysis. Catalysis of Amide Hydrolysis by the Carboxy-Group of Substituted Maleamic Acids," *J. Chem. Soc. Perk. Trans. 2* 9:1206-1214.

Kolb et al. (Jun. 1, 2001) "Click Chemistry: Diverse Chemical Function from a Few Good Reactions," *Angew Chem. Int. Ed.* 40(11):2004-2021.

Lahann et al. (2002) Reactive Polymer Coatings: A Platform for Patterning Proteins and Mammalian Cells onto a Broad Range of Materials, *Langmuir* 18(9):3632-3638.

Lahann et al. (2003) *Anal. Chem.* 75:2117-2122.

Lavalle et al. (2004) "Direct Evidence for Vertical Diffusion and Exchange Processes of Polyanions and Polycations in Polyelectrolyte Multilayer Films," *Macromolecules* 37(3):1159-1162.

Lee et al. (2007) "A Protein Nanocarrier from Charge-Conversion Polymer in Response to Endosomal pH," *J. Am. Chem. Soc.* 129(17):5362-5363.

Li et al. (2004) "Multilayer Biomimetics: Reversible Covalent Stabilization of a Nanostructured Biofilm," *Biomacromolecules* 5(5):1667-1670.

Liang et al. (2004) "Multilayer Assembly and Patterning of Poly(p-phenylenecinylene)s via Covalent Coupling Reactions," *Langmuir* 20(22):9600-9606.

Nolte et al. (2004) "Creating Effective Refractive Index Gradients Within Polyelectrolyte Multilayer Films: Molecularly Assembled Rugate Filters," *Langmuir* 20(8):3304-3310.

Picart et al. (Oct. 1, 2002) "Molecular Basis for the Explanation of the Exponential Growth of Polyelectrolyte Multilayers," *Proc. Nat. Acad. Sci.* USA 99(20):12531-12535.

Picart et al. (Nov. 2005) "Controlled Degradability of PolySaccharide Multilayer Films In Vitro and In Vivo," *Adv. Funct. Mater.* 15(11):1771-1780.

Richardson et al. (2001) "Polymeric System for Dual Growth Factor Delivery," *Nat. Biotechnol.* 19:1029-1034.

Richert et al. (2004) "Improvement of Stability and Cell Adhesion Properties of Polyelectrolyte Multilayer Films by Chemical Cross-Linking," *Biomacromolecules* 5(2):284-294.

Richert et al. (2004) "Layer by Layer Buildup of Polysaccharide Films: Physical Chemistry and Cellular Adhesion Aspects," *Langmuir* 20(2):448-458.

Rozema et al. (2003) "Endosomolysis by Masking of a Membrane-Active Agent (EMMA) for Cytoplasmic Release of Macromolecules," *Bioconjugate Chem.* 14(1):51-57.

Rozema et al. (Aug. 7, 2007) "Dynamic PolyConjugates for Targeted in Vivo Delivery of siRNA to Hepatocytes," *Proc. Nat. Acad. Sci* USA 104(32):12982-12987.

Saltzman et al. (Mar. 2002) "Building Drug Delivery into Tissue Engineering Design," *Nat. Rev. Drug Discov.* 1(3):177-186.

Santini et al. (Jan. 29, 1999) "A Controlled-Release Microchip," *Nature* 397:335-338.

Schoeler et al. (2003) "Growth of Multilayer Films of Fixed and Variable Charge Density Polyelectrolytes: Effect of Mutual Charge and Secondary Interactions," *Macromolecules* 36(14):5258-5264.

Serizawa et al. (2003) "Time-Controlled Desorption of Ultrathin Polymer Films Triggered by Enzymatic Degradation," *Angew Chem. Int. Ed.* 42(10):1147-1150.

Serizawa et al. (2002) "Thermoresponsive Ultrathin Hydrogels Prepared by Sequential Chemical Reactions," *Macromolecules* 35(6):2184-2189.

Shetty et al. (1980) "Ready Separation of Proteins from Nucleoprotein Complexes by reversible Modification of Lysine Residues," *Biochem. J.* 191:269-272.

Sukhishvili et al. (2002) "Layered, Erasable Polymer Multilayers Formed by Hydrogen-Bonded Sequential Self-Assembly," *Macromolecules* 35(1):301-310.

Sukhishvili et al. (2000) "Layered, Erasable, Ultrathin Polymer Films," *J. Am. Chem. Soc.* 122(39):9550-9551.

Sun et al. (2000) "Covalently Attached Multilayer Assemblies by Sequential Adsorption of Polycationic Diazo-Resins and Polyanionic Poly(acrylic acid)," *Langmuir* 16(10):4620-4624.

Wood et al. (2005) "Tunable Drug Release from Hydrolytically Degradable Layer-by-Layer Thin Films," *Langmuir* 21:1603-1609.

Xie et al. (Jan. 5, 1999) "Design of Reactive Porous Polymer Supports for High Throughput Bioreactors: Poly(2-vinyl-4,4-dimethylazlactone-co-acrylamide-co-ethylene dimethacrylate) Monoliths," *Biotechnol. Bioeng.* 62(1):30-35.

Yang et al. (2004) "Mechanistic Study of the Anchoring Behavior of Liquid Crystals Supported on Metal Salts and Their Orientational Responses to Dimethyl Methylphoshonate," *J. Phys. Chem. B* 108(52):20180-20186.

Yang et al. (2002) "Micropatterning of Polymer Thin Films with pH-Sensitive and Cross-Linkable Hydrogen-Bonded Polyelectrolyte Multilayers," *J. Am. Chem. Soc.* 124(10):2100-2101.

Zhang et al. (2002) *Colloid Surface A* 198:439-442.

Zhang et al. (2003) "Fabrication of Stable Hollow Capsules by Covalent Layer-by-Layer Self-Assembly," *Macromolecules* 36(11):4238-4240.

\* cited by examiner

CHARGE-DYNAMIC POLYMERS AND DELIVERY OF ANIONIC COMPOUNDS

CROSS-REFERENCES TO RELATED APPLICATIONS

This application claims priority to U.S. Provisional Application No. 60/486,107 filed Jul. 9, 2003, the entire disclosure of which is incorporated herein by reference and for all purposes as if fully set forth herein.

FIELD OF THE INVENTION

The present invention relates to dynamic charge state cationic polymers that are useful for delivery of anionic molecules and methods using the polymers.

BACKGROUND OF THE INVENTION

The safe and efficient delivery of DNA to cells presents a formidable challenge and an obstacle to the clinical success of gene therapy. Anderson, W. F. (1998) Human Gene Therapy. Nature, 392 Suppl. 25-30; Verma, I. M.; Somia, N. (1997) Gene Therapy—Promises, Problems, and Prospects. Nature, 389, 239-242; Crystal, R. G. (1995) Transfer of Genes to Humans: Early Lessons and Obstacles to Success. Science, 270, 404-410. Synthetic polymers have been investigated widely as gene delivery agents and are generally viewed as long-term alternatives to viruses due to their low immunogenicities and the ease with which they can be structurally modified. Luo, D.; Saltzman, W. M. (2000) Synthetic DNA Delivery Systems. Nat. Biotechnol., 18, 33-37. Cationic polymers are particularly useful in this context because they form conjugates with negatively charged DNA, and the incorporation of new design elements into cationic polymers has resulted in advances toward functional gene delivery systems. Despite extensive work, however, polymers remain far less efficient than their viral counterparts.

For efficient gene transfer and expression to occur, a gene delivery agent (or vector) should overcome numerous intracellular barriers to transfection. Luo, D.; Saltzman, W. M. (2000) Synthetic DNA Delivery Systems. Nat. Biotechnol., 18, 33-37. For example, a vector should be able to: 1) condense DNA into stabilized, nanometer-scale structures, 2) target cells and stimulate internalization, 3) prevent the degradation of DNA inside the cell, 4) target the cell nucleus, and 5) release DNA in the nucleus so that it is available for transcription. Progress has been made toward many of these barriers—cationic polymers are used to condense DNA into 50 to 200 nm particles (barrier 1), conjugation with cell-specific ligands can be used to target complexes and stimulate uptake (barrier 2), the incorporation of pH-buffering functionality into synthetic polymers provides protection against acidic intracellular environments (barrier 3), and the nuclear membrane has been "breached" (barrier 4). Kabanov, A. V.; Felgner, P. L.; Seymour, L. W., in Self-Assembling Complexes for Gene Delivery: From Laboratory to Clinical Trial, John Wiley and Sons, New York, 1998; Putnam, D.; Gentry, C. A.; Pack, D. W.; Langer, R. (2001) Polymer-Based Gene delivery with Low Cytotoxicity By a Unique Balance of Side-Chain Termini. Proc. Natl. Acad. Sci. USA, 98, 1200-1205; Midoux, P.; Monsigny, M. (1999) Efficient Gene Transfer by Histidylated Polylysine/pDNA Complexes. Bioconjugate Chem., 10, 406-411; Boussif, O.; Lezoualc'H, F.; Zanta, M. A.; Mergny, M. D.; Scherman, D.; Demeneix, B.; Behr, J. P. (1995) A Versatile vector for Gene and Oligonucleotide Transfer Into Cells in Culture and In Vivo—Polyethyleneimine Proc. Natl. Acad. Sci. USA, 92, 7297-7301; Benns, J. M.; Choi, J.; Mahato, R. I.; Park, J.; Kim, S. W. (2000) pH-sensitive Cationic Polymer Gene Delivery Vehicle: N-Ac-poly(L-histidine)-graft-poly(L-lysine) Comb Shaped Polymer. Bioconjugate Chem., 11, 67-645; Wolff, J. A.; Sebestyen, M. G. (2001) Nuclear Security Breached. Nature Biotechnol., 19, 1118-1120; Rebuffat, A.; Bernasconi, A.; Ceppi, M.; Wehrli, H.; Verca, S. B.; Ibrahim, M.; Frey, B. M.; Frey, F. J.; Rusconi, S. (2001) Selective Enhancement of Gene transfer by Steroid-Mediated Gene Delivery. Nature Biotechnol., 9, 1155-1161. These recent successes have fueled hopes of a "grand design" in which individual design elements could be assembled to create synthetic vectors that functionally mimic viruses. Wolff, J. A. (2002) The "Grand" Problem of Synthetic Delivery. Nature Biotechnol., 20, 768-769. However, the breach of early barriers to transfection simply places increased significance on downstream barriers, and the design of materials to address the fifth and final barrier—the efficient and timely separation of polymer from DNA in the nucleus—has not been adequately addressed.

This "ultimate" barrier to efficient transfection presents a challenging problem from a design perspective, as designing methods to surmount it can introduce a functionality that is contrary to that required for efficient DNA condensation (i.e., barrier 1). Kircheis, R.; Wightman, L.; Wagner, E. (2001) Design and Gene Delivery Activity of Modified Polyethyleneimines. Advanced Drug Delivery Reviews, 53, 341-358. Cationic polymers spontaneously self-assemble with anionic DNA through electrostatic interactions to form condensed interpolyelectrolyte complexes—a process that is driven entropically by the elimination of small salts (e.g., NaCl) formed upon complex formation. Kabanov, A. V.; Feigner, P. L.; Seymour, L. W., in Self-Assembling Complexes for Gene Delivery: From Laboratory to Clinical Trial, John Wiley and Sons, New York, 1998.

Cationic polymers undergo self-assembly with anionic plasmid DNA to form condensed complexes. The reverse of this process—the intracellular dissociation of DNA from condensed interpolyelectrolyte complexes—appears to be unfavorable under physiological conditions and presents a substantial obstacle to efficient gene delivery.

Although the effects of pH, temperature, salt concentration, and molecular weight on the dissociation of model interpolyelectrolyte complexes are generally well understood, the mechanisms through which dissociation occurs for polymer complexes in the cytoplasm or nucleus of a cell are currently unclear. Bronich, T. K.; Nguyen, H. K.; Eisenberg, A.; Kabanov, A. V. (2000) Recognition of DNA Topology in Reactions Between Plasmid DNA and Cationic Polymers. J. Am. Chem. Soc., 122, 8339-8343. That meaningful levels of transfection are observed using polymeric vectors suggests that dissociation does occur, presumably mediated by ion exchange with other intracellular polyelectrolytes. However, recent analytical experiments suggest that DNA/polycation complexes are stable toward intracellular dissociation and that the inefficiency of this "unpackaging" process presents a substantial physical barrier to transfection. Godbey, W. T.; Wu, K.; Mikos, A. G. (1999) Tracking the Intracellular Path of Poly(ethyleneimine)/DNA Complexes for Gene Delivery. Proc. Natl. Acad. Sci. USA, 96, 5177-5181; Schaffer, D. V.; Fidelman, N. A.; Dan, N.; Lauffenburger, D. A. (2000) Vector Unpackaging as a Potential Barrier for Receptor-Mediated Polyplex Gene Delivery. Biotechnol. Bioeng., 67, 598-606.

SUMMARY OF THE INVENTION

The present invention provides a dynamic charge state cationic polymer, or more simply a polymer, that includes a polymeric backbone formed from monomeric units. One or more removable functional group is/are attached to the polymeric backbone. The dynamic charge state cationic polymer has a cationic charge density which is a characteristic of the polymeric backbone and the functional group attached to the polymeric backbone. The cationic charge density of the dynamic charge state cationic polymer decreases when the one or more of the removable functional group(s) is/are removed from the dynamic charge state cationic polymer. The present polymers can also be part of a copolymer where only one segment of the copolymer is the dynamic charge state cationic polymer. In some embodiments, the polymeric backbone comprises a polyamine, such as polyethyleneimine, polylysine, polyomithine or poly/lysine/ornithine. In some embodiments, the polymers contain side chains that have primary, secondary or tertiary amines. Other examples of suitable polymeric backbones include poly(propylene imine), poly(allyl amine), poly(vinyl amine), poly(amidoamine) (PAMAM), and dendrimers that are functionalized with terminal amine groups. Further examples include acrylate or methacrylate polymers such as poly(2-aminoethyl methacrylate), and the like. In some embodiments where amine functional groups are present in the polymer, primary amines may be functionalized either once or twice to provide a polymer that has a net negative charge once removal of the one or more removable functional group is complete. In the present polymers, the polymeric backbone can be linear, branched or hyperbranched, particularly when the backbone is polyethyleneimine.

In some embodiments, at least one of the one or more removable functional group(s) is a hydrolyzable group, such as a pendant ester. The one or more removable functional group(s) may also include a labile linkage, such as an ester, an anhydride, an orthoester, a phosphoester, an acetal, or an amide. In certain embodiments, the polymer has the formula:

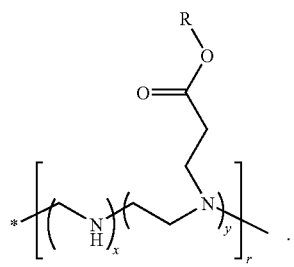

When the polymer has the formula shown above, n may be an integer ranging from 5 to 100,000, x is an integer, and the mole percent of y ranges from 10 percent to 100 percent based on the total of x and y. In the present compounds, the identity of R is not particularly limited. For example, R can be an alkyl, alkenyl, alkynyl, cycloalkyl, heterocyclic, aryl, or a heteroaryl group. R may also be carbon-containing, heteroatom-containing (N, S, O, P, etc.), linear, branched, an amino, an alkylamino, a dialkylamino, a trialkylamino, aryl, a heterocyclyl, a cyano, an amide, a carbamoyl, or the like. When the R group is alkyl, R can be methyl, ethyl, propyl, butyl, pentyl, hexyl, or combinations thereof.

In some embodiments, the polymers of the invention are biodegradable and biocompatible.

Other examples of polymers include compounds of the following formula:

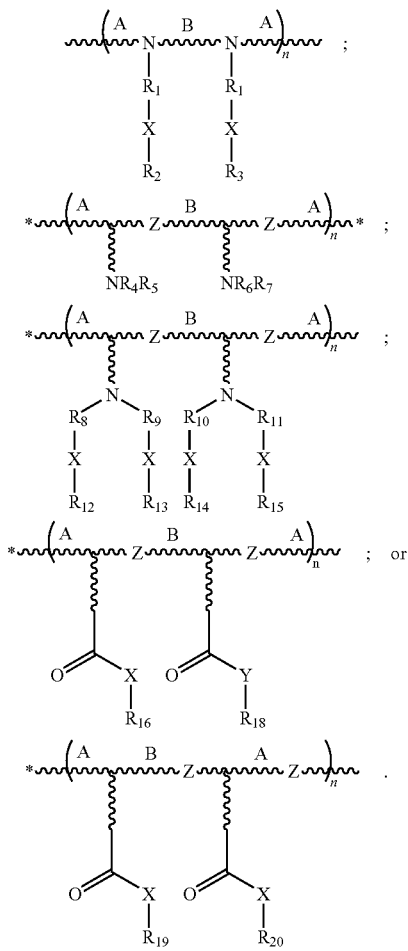

In the above polymers, n may be an integer of from 5 to 100,000, A and B are linkers which may be the same or different and can be any substituted or unsubstituted, branched or unbranched chain of carbon atoms or heteroatoms; $R_1$ may be a linker group or a covalent bond; X may be the same or different and can be a labile linkage, which, in some instances is negatively charged after cleavage; Y can be a linkage that is generally not as labile as X; $R_2$ through $R_7$ and $R_{12}$ through $R_{20}$ can have the value for R listed above and can be the same or different; $R_8$, $R_9$, $R_{10}$ and $R_{11}$ are linkers or covalent bonds; and Z can be a covalent bond or a degradable linkage. In some embodiments X is an ester linkage and Y is an amide linkage, such as $NR_{17}$. In some embodiments, $R_{16}$ is $NR_{21}R_{22}$, $R_{17}$ is H, and $R_{18}$ is $NR_{23}R_{24}$. In some embodiments, $R_{19}$ is $NR_{25}R_{26}$ and $R_{20}$ is $NR_{27}R_{28}$. $R_{21}$ through $R_{28}$ can have the value for R listed above and can be the same or different. When Z is a covalent bond, the polymer backbone is non-degradable. The linkers A and B can be linkers that contain carbon atoms or heteroatoms (e.g., nitrogen, oxygen, sulfur, etc.). Typically, these linkers are 1 to 30 atoms long, more preferably 1 to 15 atoms long. The linkers may be substituted with various substituents including, but not limited to, hydrogen atoms, and alkyl, alkenyl, alkynyl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, and ureido groups. As would be appreciated by one of skill in this art, each of these groups may in turn be substituted. For some polymers the ester bond will generally be readily hydrolyzable whereas the amide bond is not readily hydrolyzable. This configuration allows more control over the change of cationic charge density of the polymer by altering the ratio of ester bonds and amide bonds present in the one ore more removable functional group.

In the present polymers, the mole percent of the monomers comprising the polymeric backbone substituted with the one or more removable functional group range from 10 to 100 percent or from about 10 percent to about 100 percent. In additional embodiments, the mole percent of the monomers attached to the removable functional group may range from about 30 percent to 100 percent, 50 percent to 100 percent or 70 percent to 100 percent. The polymers of the present invention may have any desired molecular weight, such as from 1,000 to 100,000 grams/mole, or from about 2,000 to 50,000 grams/mole. The dynamic charge state cationic polymer can be associated with a ligand facilitating the delivery of the polymer to a specific target, such as a target cell. The present polymers can also be part of a copolymer, which can be composed of any other polymers, for example a polymer such as PEG or PEO which are commonly used to give stability toward protein adsorption. The present polymer is generally cationic, but different functional groups attached to the polymer can render the polymer zwitterionic. To impart a cationic charge to the polymer, the polymeric backbone or the attached functional groups can be positively charged. The present polymer may also be capable of buffering changes in pH which results from the make-up of the polymer backbone and/or the attached functional groups.

The present dynamic charge state cationic polymers may be non-immunogenic, non-toxic or both non-immunogenic and non-toxic. In the present polymers, the polymeric backbone can be degradable or nondegradable. The present polymers do not require that the degradation of the backbone occur at the same time as the shift in cationic charge. One skilled in the art will recognize that the measure of degradability will be commensurate with the environmental conditions and desired properties for any particular application for the present polymers. As one non-limiting example, for biomedical uses of the present polymers, the present invention contemplates polymers that degrade in a desired time frame (from an hour to a week to a month to a year) under physiological conditions typically found in the body or in a cell or cell compartment [e.g., pH ranges from about 5.0 (endosomal/lysosomal) to 7.4 (extracellular and cytosol), a temperature of about 37° C. and an ionic strength of a typical physiological solution (generally around 130-150 mM NaCl, for example)]. In the present invention, the degradability of the polymer can be measured by a variety of methods, including, but not limited to, GPC (gel permeation chromatography).

The present invention also provides the present polymers complexed with one or more anionic molecules thereby forming an interpolyelectrolyte complex. Suitable anionic molecules may be naturally occurring, synthetic, or both. In some embodiments, suitable examples of anionic molecules include nucleic acids, such as RNA, DNA, and analogs thereof. In other embodiments, the anionic molecule is a synthetic polyanion. In still other embodiments, the polymers of the invention are complexed with an anionic molecule such as nucleic acids, such as RNA, DNA, or analogs thereof, and a synthetic polyanion. When the anionic molecule is a nucleic acid, the nucleic acid can have the sequence of a nucleic acid molecule of interest or its complement. As such, the nucleic acid can encode for a protein or a functional fragment thereof or be useful in antisense treatment or RNA interference. In some embodiments, the nucleic acid is a plasmid.

In other embodiments, the anionic molecule or agent may be a therapeutic molecule, diagnostic molecule, peptide, or carbohydrate, for example a macromolecular carbohydrate such as heparin.

The interpolyelectrolyte complex may have any desired size depending upon the intended use of the interpolyelectrolyte complex. For example, when the interpolyelectrolyte complex is used for nucleic acid delivery to a cell, the interpolyelectrolyte complex can be 50 nm to about 400 nm, or from about 50 to about 250 nanometers, in size. In other embodiments, the interpolyelectrolyte complex may be provided in a layered complex made up of one or more layers of the dynamic charge state cationic polymer and one or more layers of the anionic molecule.

In some embodiments, the present polymer or interpolyelectrolyte complex may be provided in a biologically compatible solution or a biological solution. Further, the polymer may be provided with a pharmaceutically acceptable excipient or another completely different polymer (e.g., another cationic polymer) which could be an "excipient" or could have an added function. Accordingly, the present compounds include pharmaceutical compositions that include any of the polymers or mixtures described herein.

The present invention also provides methods for delivering an anionic compound to a cell or tissue. The present methods involve contacting a composition that includes a present interpolyelectrolyte complex with a target cell thereby allowing the target cell to uptake the composition. The polymer of the present invention is designed such that when the interpolyelectrolyte complex enters the target cell, one or more of the removable functional group(s) is/are removed from the dynamic charge state cationic polymer which decreases the cationic charge density of the dynamic charge state cationic polymer. The decrease in the cationic charge density of the polymer may be caused by the introduction of anionic charges which promotes dissociation of the interpolyelectrolyte complex into the dynamic charge state cationic polymer and the anionic molecule allowing for delivery of the anionic molecule to the target cell or cell compartment, such as an endosome, cytosol or nucleus of the cell. In some methods, at least one of the one or more of the removable functional group(s) is removed from the dynamic charge state cationic polymer in a nucleus, endosome or cytosol of the target cell. In this manner, the interpolyelectrolyte complex may dissociate primarily in the desired compartment of the target cell and deliver the anionic molecule to the target cell compartment. The present methods may also involve providing the interpolyelectrolyte complex and/or preparing the interpolyelectrolyte complex. Generally, the interpolyelectrolyte complex will be prepared by mixing the dynamic charge state cationic polymer with the anionic molecule thereby allowing formation of the interpolyelectrolyte complex. In the methods where the anionic molecule is DNA, the DNA may be delivered to the nucleus of the cell so that it is stably incorporated into the genome of the target cell. In other embodiments, the DNA is not stably incorporated into the genome of the target cell.

In the present methods, the target cell or tissue can be in vitro or in vivo. Where the target cell or tissue is in vivo, the interpolyelectrolyte complex may be administered to a mammal. In some embodiments of the present methods, the cell is a eukaryotic cell.

In the present methods and polymers, removal of the one or more of the removable functional group(s) from the dynamic charge state cationic polymer may be at least partially hydrolytic, partially enzymatic and/or partially photolytic removal. The present polymers and methods may also be designed so that the removal of the one or more of the removable functional group(s) from the dynamic charge state cationic polymer occurs at a substantially constant rate or does not occur at a constant rate.

The present invention also provides kits containing the present polymers.

The invention also provides methods of preparing the polymers and methods of preparing microspheres and other pharmaceutical compositions containing the polymers.

In yet another aspect of the invention, the polymers are used to form nanometer-scale complexes with nucleic acids. The polynucleotide/polymer complexes may be formed by adding a solution of polynucleotide to a vortexing solution of the polymer at a desired DNA/polymer concentration. The weight to weight ratio of polynucleotide to polymer may range from 1:0.1 to 1:50, preferably from 1:1 to 1:20, more preferably from 1:1 to 1:10. The cationic polymers condense the polynucleotide into soluble particles typically 50-500 nm in size. These polynucleotide/polymer complexes may be used in the delivery of polynucleotides to cells. In some embodiments, these complexes are combined with pharmaceutical excipients to form pharmaceutical compositions suitable for delivery to animals including humans.

In another aspect of the invention, the polymers are used to encapsulate therapeutic, diagnostic, and/or prophylactic agents including polynucleotides to form microparticles. Typically these microparticles are one or more orders of magnitude larger than the polynucleotide/polymer complexes. The microparticles range from 1 micrometer to 500 micrometers. In some such embodiments, the microparticles allow for the delivery of labile small molecules, proteins, peptides, and/or polynucleotides to an individual. The microparticles may be prepared using any of the techniques known in the art to make microparticles, such as, for example, double emulsion and spray drying. In some embodiments, the microparticles may be used for pH-triggered delivery of the encapsulated contents due to the pH-responsive nature of the polymers (i. e., being more soluble at lower pH).

DETAILED DESCRIPTION OF THE INVENTION

Figure 1:
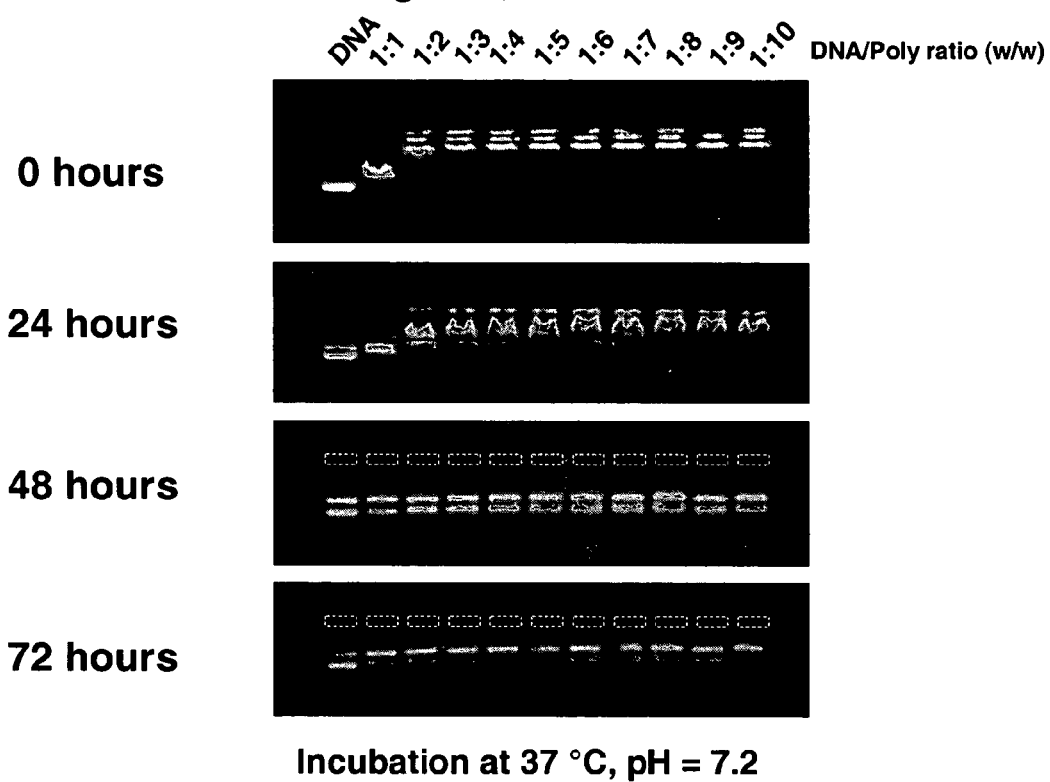
FIGS. 1-11 show the visualization of polycation/DNA interpolyelectrolyte complex formation and subsequent release of DNA from destabilized interpolyelectrolyte complexes of the present invention.
Figure 2:
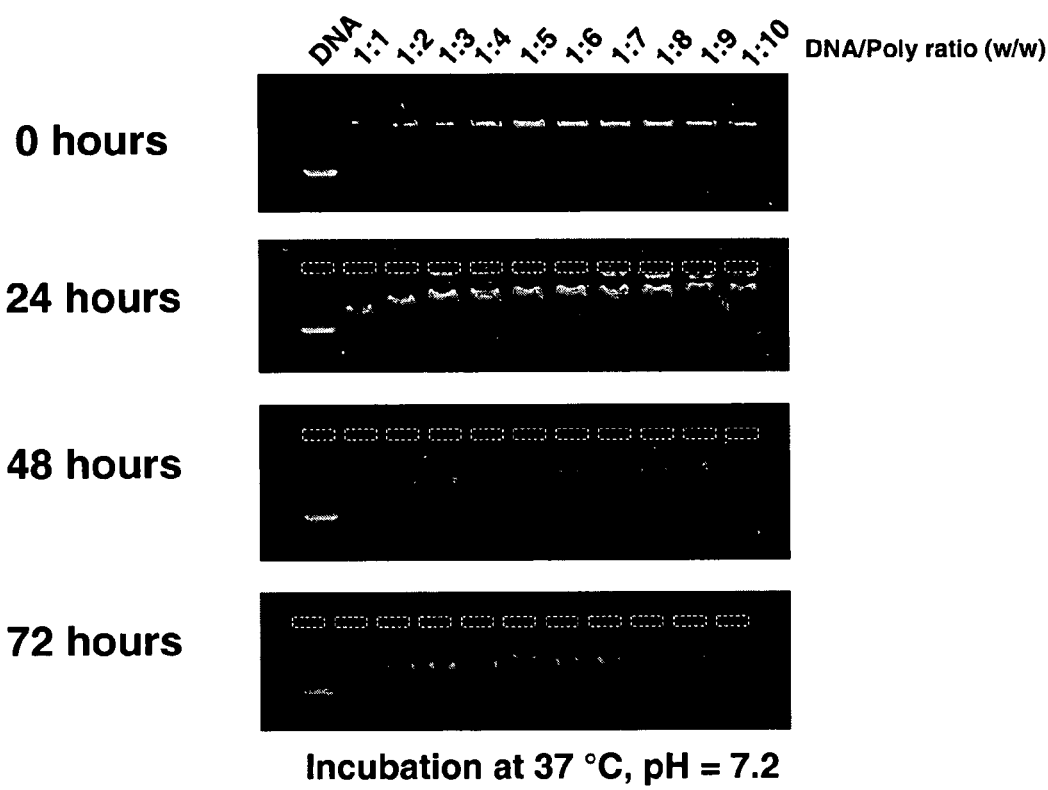
Figure 3:
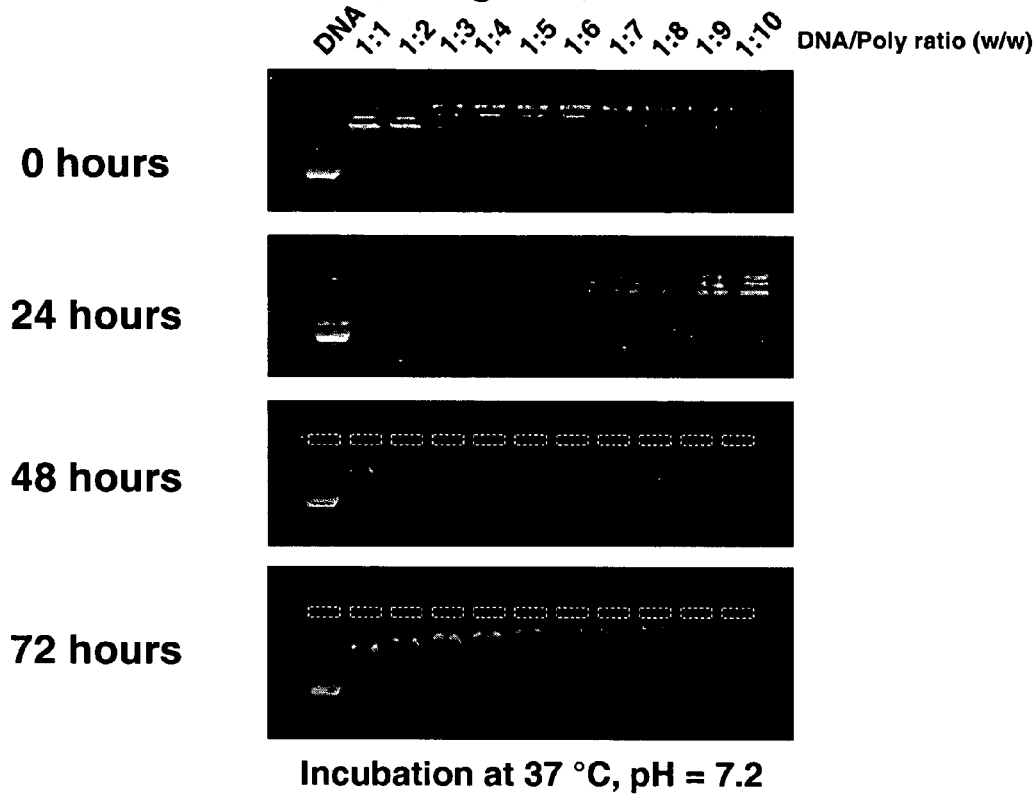
Figure 4:
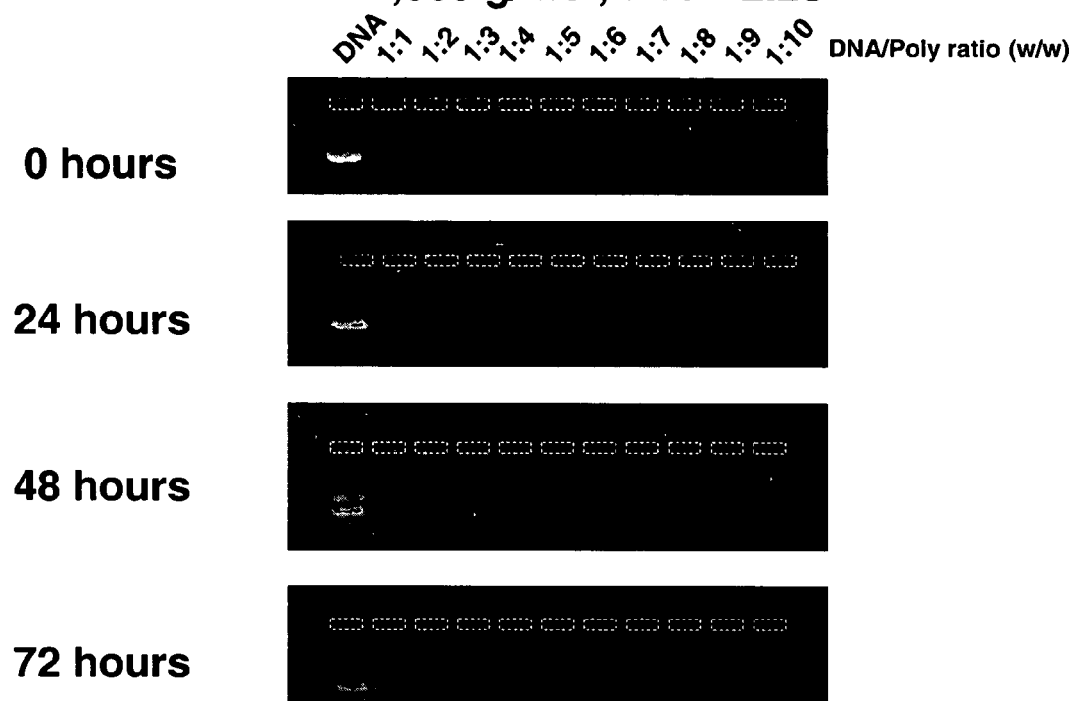
Figure 5:
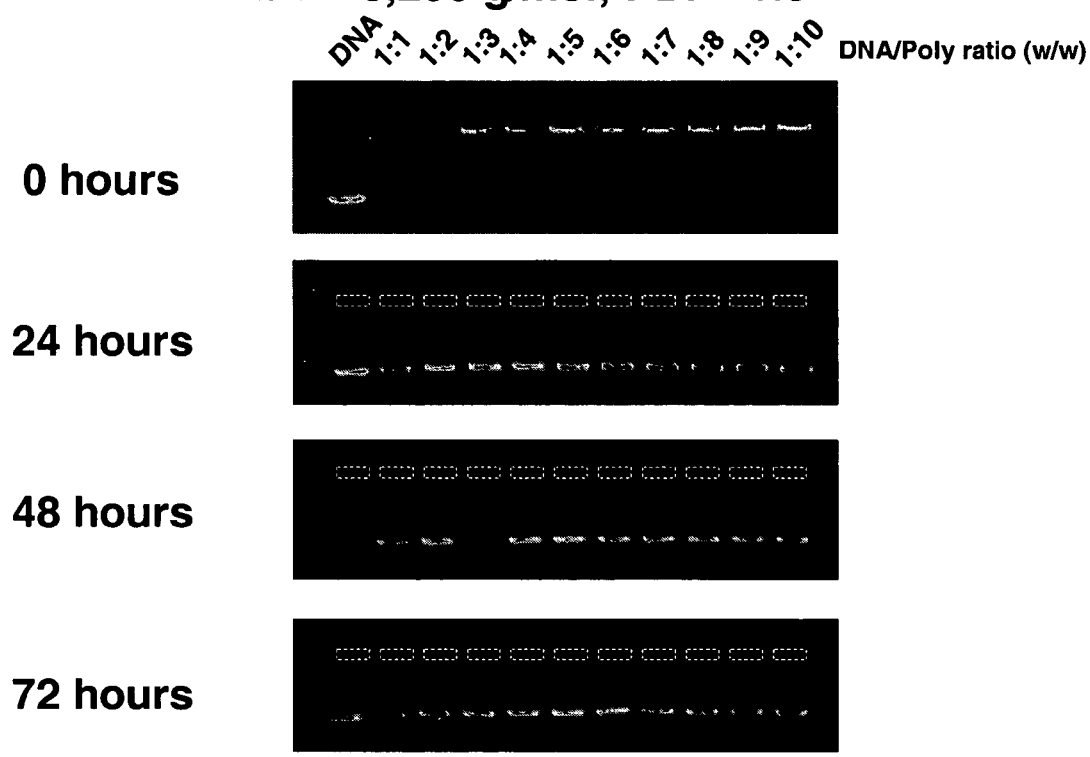
Figure 6:
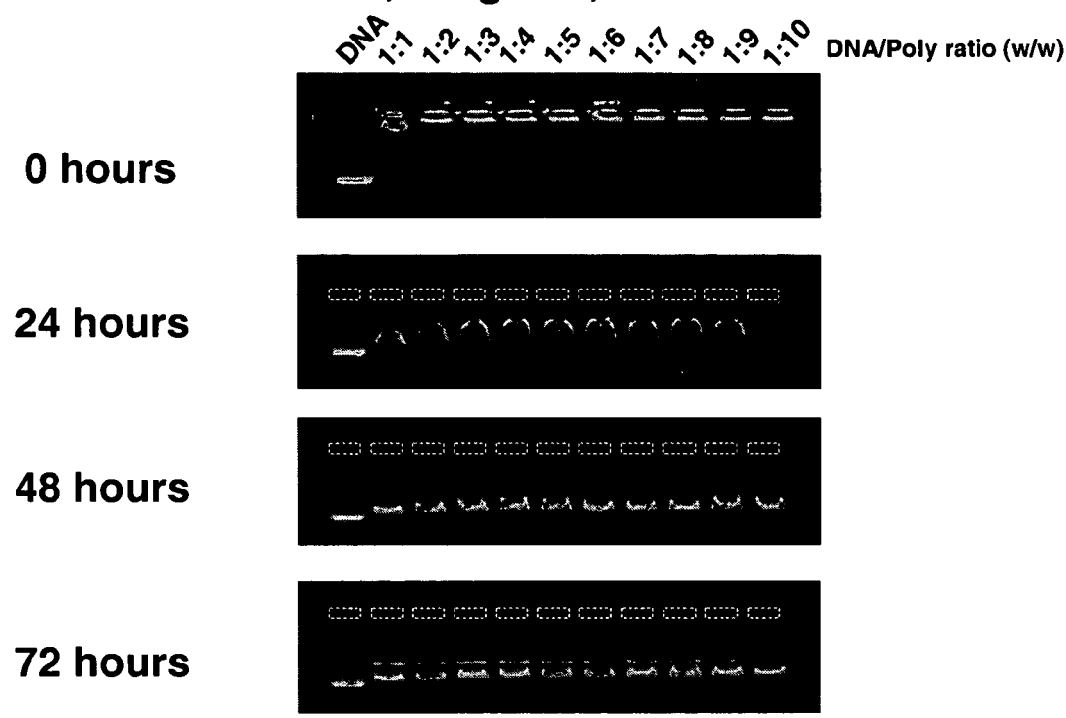
Figure 7:
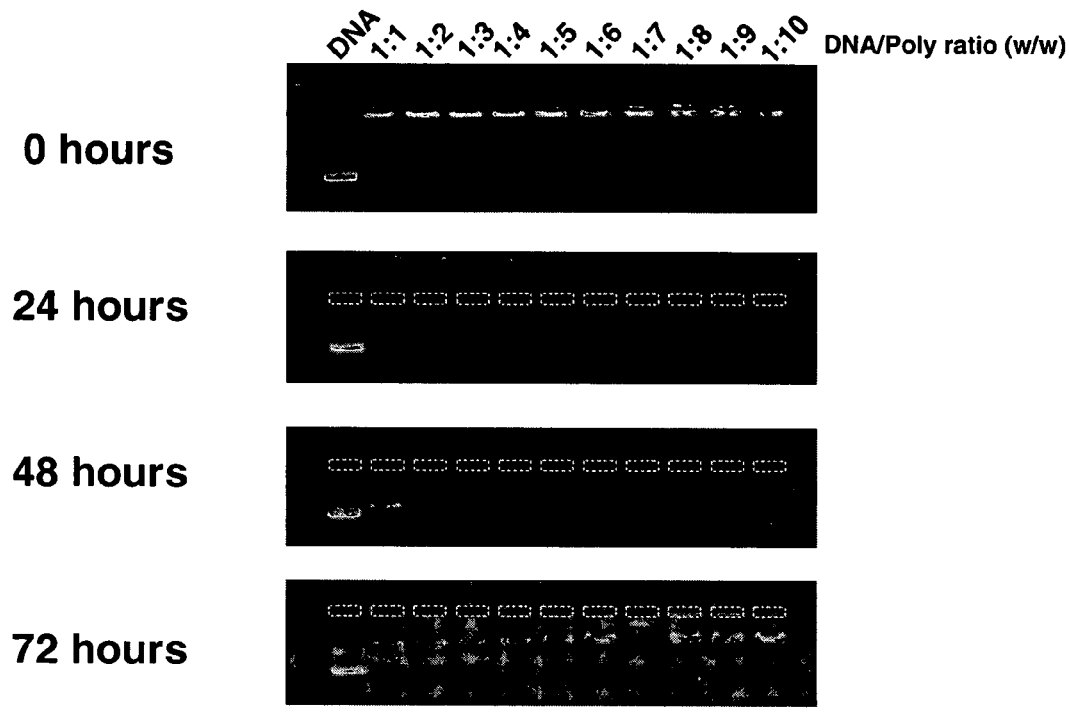
Figure 8:
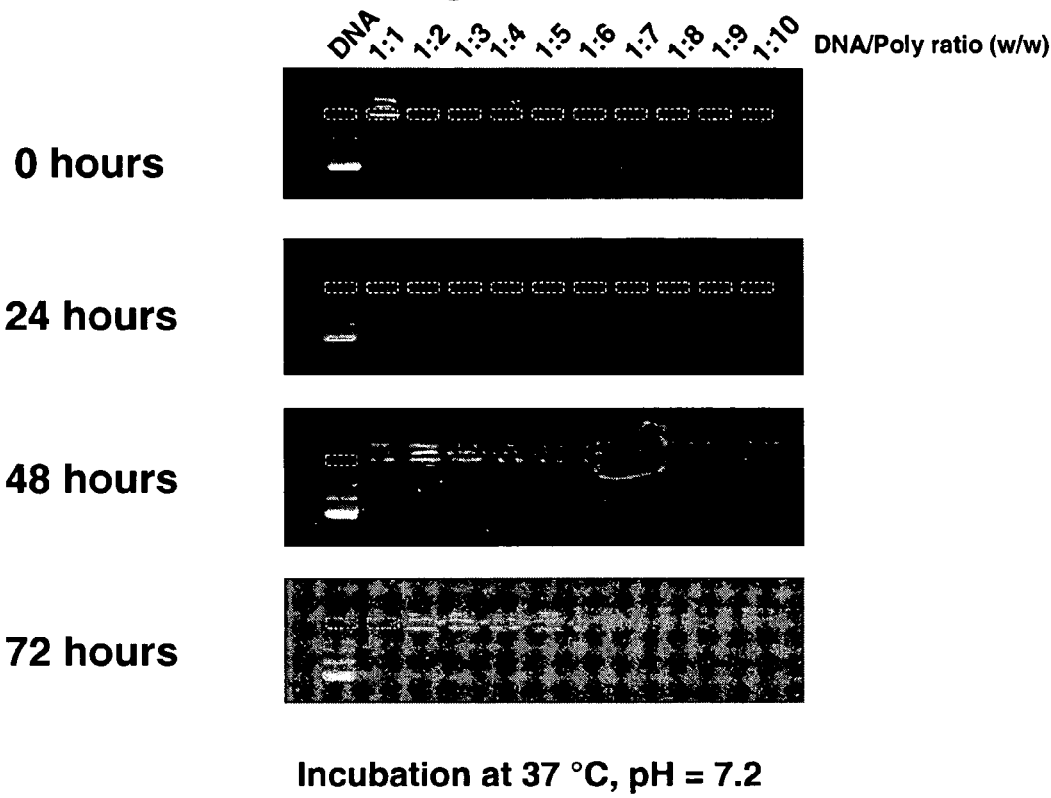
Figure 9:
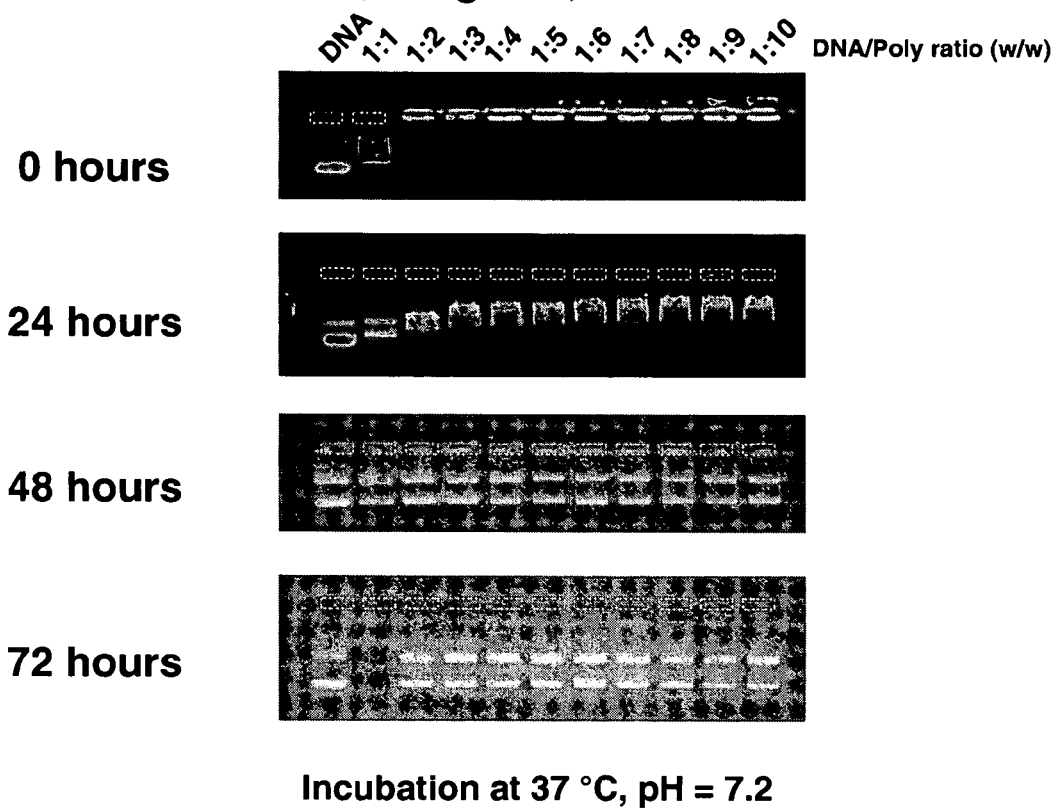
Figure 10:
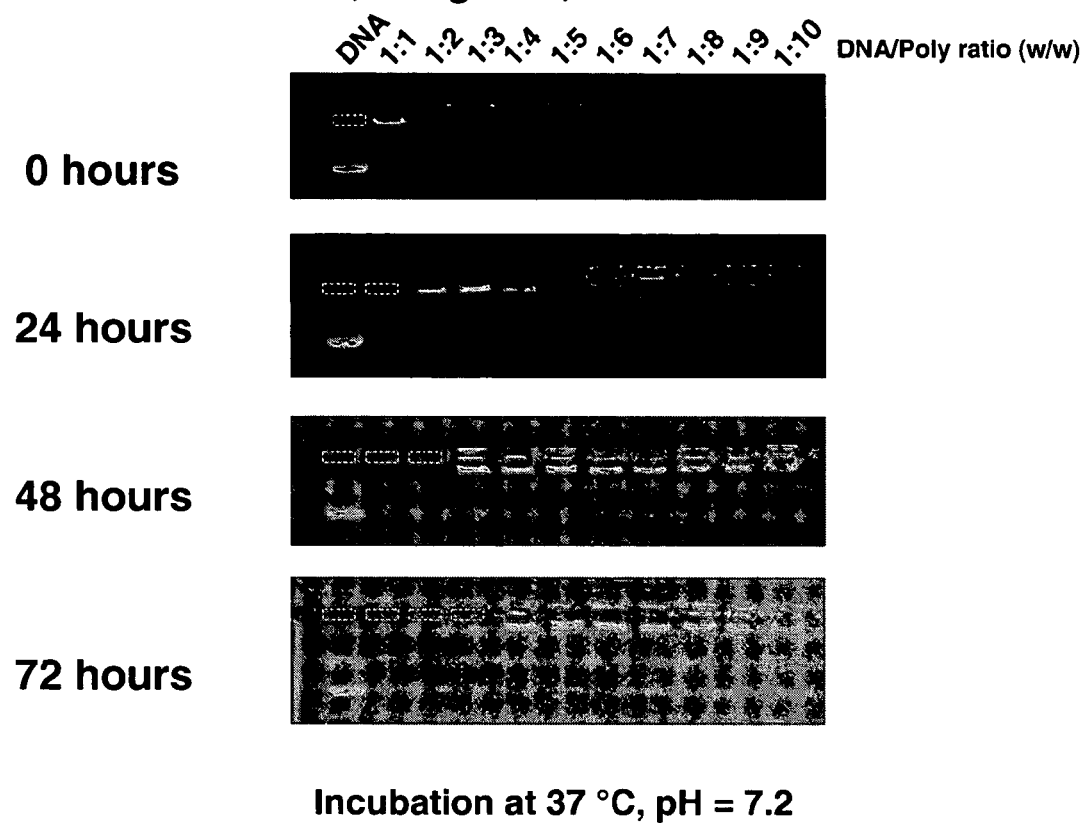

The present invention focuses on providing polymers that address the final physical barrier to efficient delivery—the timely intracellular dissociation of DNA from polymer/DNA interpolyelectrolyte complexes. The general approach of the present invention is based on the synthesis of cationic polymers that undergo dynamic changes in charge states (i.e., from cationic to "less cationic" or zwitterionic) to trigger the "unpackaging" of anionic molecules, such as DNA, from interpolyelectrolyte complexes. In one embodiment, the synthetic design is based on the introduction of side-chain esters to linear poly(ethylene imine) via conjugate addition chemistry. Without limiting the scope of the invention, it is believed that the dynamic introduction of carboxylate groups into these polymers, which occurs via the gradual hydrolysis of pendant ester groups, effectively lowers the cationic charge densities of the polymers and promotes the dissociation of polymer/anion complexes. The disclosed polymers undergo a shift in charged states as a function of time to initiate the efficient and timely unpackaging of DNA from condensed particles in the intracellular environment.

Affecting the timely intracellular dissociation of polycation/anionic complexes is an important and unsolved problem. The present polymers address this final physical barrier to anion delivery and can lead to effective new formulations for anion delivery and, importantly, allow existing solutions to earlier barriers to be exploited more fully. Prior research has generally approached this problem through the synthesis of hydrolytically degradable polycations or by the development of disulfide-crosslinked networks that use exposure to reductive intracellular environments to trigger degradation and enhance polymer dissociation. Peterson, H.; Merdan, T.; Kunath, K.; Fischer, D.; Kissel, T. (2002) Poly(ethylene-imine-co-L-lactamide-co-succinamide): A Biodegradable Polyethyleneimine Derivative with an Advantageous pH-Dependent Hydrolytic Degradation for Gene Delivery. Bioconjugate Chem., 13, 812-821; Wang, J.; Mao, H.; Leong, K. W. (2001) A Novel Biodegradable Gene Carrier Based on Polyphosphoester. J. Am. Chem. Soc., 123, 9480-9481; Lim, Y.; Kim, C.; Kim, K.; Kim, S. W.; Park, J. (2000) Development of a Safe Gene Delivery System Using Biodegradable Polymer, Poly[α-(4-aminobutyl)-L-glycolic acid]. J. Am. Chem. Soc., 122, 6524-6525; Lynn, D. M.; Langer, R. (2000) Degradable Poly(β-Amino Esters): Synthesis, Characterization, and Self-Assembly with Plasmid DNA J. Am. Chem. Soc., 122, 10761-10768; Putnam, D.; Langer, R. (1999) Poly(4-hydroxy-1-proline ester): Low-Temperature Polycondensation and Plasmid DNA Complexation. Macromolecules, 32, 3658-3662; Oupicky, D.; Parker, A. L.; Seymour, L. W. (2002) Laterally Stabilized Complexes of DNA with Linear Reducible Polycations: Strategy for Triggered Intracellular Activation of DNA Delivery Vectors. J. Am. Chem. Soc., 124, 8-9; Pichon, C.; LeCam, E.; Guérin, B.; Coulaud, D.; Delain, E.; Midoux, P. (2002) Poly[Lys-(AEDTP)]: A Cationic Polymer That Allows Dissociation of pDNA/Cationic Polymer Complexes in a Reductive Medium and Enhances Polyfection. Bioconjugate Chem., 13, 76-82; Gosselin, M. A.; Guo, W.; Lee, R. J. (2001) Efficient Gene Transfer Using Reversibly Cross-Linked Low Molecular Weight Polyethyleneimine. Bioconjugate Chem., 12, 989-994. The present invention provides a different approach, based on synthetic polymers that shift charge states dynamically to trigger the "unpackaging" of DNA from interpolyelectrolyte complexes through the introduction of repulsive electrostatic interactions. One embodiment is outlined below:

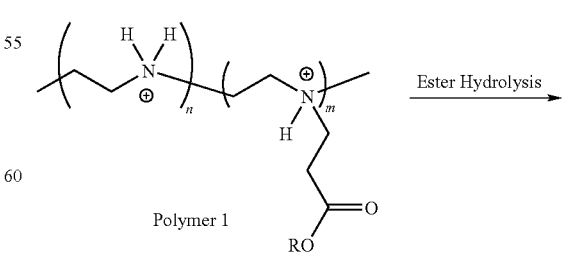

Polymer 1     Ester Hydrolysis

Approx. Charge at Physiological pH = 
(n + m) ⊕ "cationic"

-continued

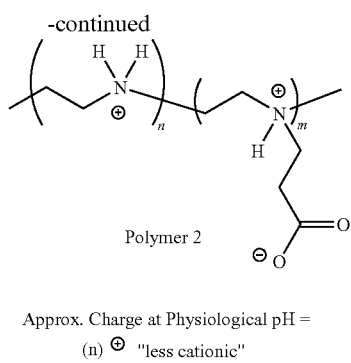

Polymer 2

Approx. Charge at Physiological pH =
(n) ⊕ "less cationic"

The above scheme demonstrates the general concept of dynamic introduction of carboxylate groups to a cationic poly(amine) via side-chain ester hydrolysis. Assuming full protonation for illustrative purposes, the overall positive charge on polymer 1 is the sum of 'n+m', and this polymer is capable of forming interpolyelectrolyte complexes with polyanions such as DNA. Hydrolysis of the ester side chains in polymer 1 (assuming complete hydrolysis of all ester side chains) introduces 'm' negative carboxylate groups and thus reduces the overall positive charge on polymer 2 to 'n', promoting dissociation of polymer complexes.

In this embodiment, the dynamic introduction of carboxylate groups into cationic polymers (via the gradual hydrolysis of pendant ester groups) effectively "neutralizes" or reduces the charge densities of these polymers and exerts a destabilizing influence that can promote the dissociation of polymer/DNA complexes. For example, the overall positive charge on polymer 1 is reduced from (n+m)+ to (n)+ upon hydrolysis (above scheme, assuming full protonation for illustrative purposes and complete hydrolysis of ester groups in polymer 2). One skilled in the art will recognize that this charge shifting capability can be readily applied to other polymers.

In some embodiments, the present polymers are based on linear poly(ethylene imine) (PEI) as the structural template from which polymers are synthesized. Linear PEI is an attractive template for several reasons: 1) it is commercially available or can be synthesized directly via the ring-opening polymerization of substituted oxazolines, 2) it is a proven gene transfer agent already capable of surmounting many "early" barriers to transfection, and 3) the linear array of secondary amines facilitates the introduction of new functionality through well defined chemistry. Odian, G., Principles of Polymerization, John Wiley and Sons, Inc., New York, 1991; Kircheis, R.; Wightman, L.; Wagner, E. (2001) Design and Gene Delivery Activity of Modified Polyethyleneimines. Advanced Drug Delivery Reviews, 53, 341-358; Yin, R.; Zhu, Y.; Tomalia, D. A. (1998) Architectural Copolymers: Rod-Shaped, Cylindrical Dendrimers. J. Am. Chem. Soc., 120, 2678-2679. The methods below can also be applied to branched or hyperbranched PEI (also an effective gene transfer agent). Boussif, O.; Lezoualc'H, F.; Zanta, M. A.; Mergny, M. D.; Scherman, D.; Demeneix, B.; Behr, J. P. (1995) A Versatile Vector for Gene and Oligonucleotide Transfer Into Cells in Culture and In Vivo—Polyethyleneimine Proc. Natl. Acad. Sci. USA, 92, 7297-7301; Kircheis, R.; Wightman, L.; Wagner, E. (2001) Design and Gene Delivery Activity of Modified Polyethyleneimines. Advanced Drug Delivery Reviews, 53, 341-358. In some embodiments, the present invention modifies polymers that are already known as effective polyanion delivery agents.

In some embodiments, the synthetic strategy is based on the conjugate addition of the secondary amines of PEI to acrylate compounds. The exhaustive functionalization of linear PEI has been demonstrated in the context of dendrimer synthesis using methyl acrylate, yielding ester-functionalized polymer 1 (R=methyl, n=0) having regularly repeating tertiary amines in the polymer backbone. Yin, R.; Zhu, Y.; Tomalia, D. A. (1998) Architectural Copolymers: Rod-Shaped, Cylindrical Dendrimers. J. Am. Chem. Soc., 120, 2678-2679.

The introduction of the alkyl ester groups in some of the present polymers may influence the pKa's and increase the steric bulk surrounding the amines, and may consequently affect the ability of the polymers to form complexes with DNA. To investigate the relationships between charge density, backbone substitution, and interpolyelectrolyte complex formation (methods described below) a family of polymers with a range of mole percent substitution (i.e., from about 10% to 100% functionalized) have been synthesized. Putnam, D.; Gentry, C. A.; Pack, D. W.; Langer, R. (2001) Polymer-Based Gene Delivery with Low Cytotoxicity by a Unique Balance of Side-Chain Termini. Proc. Natl. Acad. Sci. USA, 98, 1200-1205; Jeong, J. H.; Song, S. H.; Lim, D. W.; Lee, H.; Park, T. G. (2001) DNA Transfection Using Linear Poly(ethyleneimine) Prepared by Controlled Acid Hydrolysis of Poly(2-ethyl-2-oxazoline). J. Control. Release, 73, 391-399. Similarly, polymers with varying hydrophobicities and charge densities have been synthesized by conjugate addition to more hydrophobic acrylates (i.e., where R=ethyl, propyl, butyl, or combinations thereof). Because both transfection and the "unpackaging" of DNA from interpolyelectrolyte complexes appear to be related to polycation molecular weight (with shorter polymers tending to dissociate more readily than larger polymers), individual syntheses were conducted using PEI of different molecular weights and polydispersities to explore these relationships and optimize polymer behavior. Godbey, W. T.; Wu, K. K.; Mikos, A. G. (1999) Size Matters: Molecular Weight Affects the Efficiency of Poly (ethyleneimine) as a Gene Delivery Vehicle. J. Biomed. Mater. Res., 45, 268-275; Schaffer, D. V.; Fidelman, N. A.; Dan, N.; Lauffenburger, D. A. (2000) Vector Unpackaging as a Potential Barrier for Receptor-Mediated Polyplex Gene Delivery. Biotechnol. Bioeng., 67, 598-606.

As described above, polycations and plasmid DNA spontaneously self-assemble under physiological conditions to form nanometer-scale interpolyelectrolyte complexes. These complexes may be destabilized by exposure to high salt concentrations or by the presence of other polyelectrolytes that initiate polyion exchange processes. Bronich, T. K.; Nguyen, H. K.; Eisenberg, A.; Kabanov, A. V. (2000) Recognition of DNA Topology in Reactions Between Plasmid DNA and Cationic Polymers. J. Am. Chem. Soc., 122, 8339-8343. Agarose gel electrophoresis provides for convenient visualization of polycation/DNA interpolyelectrolyte complex formation and is used as a qualitative measure for the subsequent release of DNA from destabilized complexes. Lynn, D. M.; Langer, R. (2000) Degradable Poly(β-Amino Esters): Synthesis, Characterization, and Self-Assembly with Plasmid DNA J. Am. Chem. Soc., 122, 10761-10768; Putnam, D.; Langer, R. (1999) Poly(4-hydroxy-1-proline ester): Low-Temperature Polycondensation and Plasmid DNA Complexation. Macromolecules, 32, 3658-3662; Wang, J.; Mao, H.; Leong, K. W. (2001) A Novel Biodegradable Gene Carrier Based on Polyphosphoester. J. Am. Chem. Soc., 123, 9480-9481. To obtain more quantitative information about the biophysical interactions between DNA and the polymers synthesized above, one may also use an established fluorescence-based ethidium bromide exclusion assay to investigate the kinetics of complex destabilization. Bronich, T. K.; Nguyen, H. K.; Eisenberg, A.; Kabanov, A. V. (2000) Recognition of DNA Topology in Reactions Between Plasmid DNA and Cationic Polymers. J. Am. Chem. Soc., 122, 8339-8343.

The kinetics of ester hydrolysis and interpolyelectrolyte complex disruption of some of the present polymers was evaluated over a range of pH, temperature, and salt concentration, focusing on those conditions likely to be encountered by these materials during transfection (e.g., 37° C., 150 mM NaCl, and pH values ranging from 5.1 to 7.2 to approximate the pH within endosomal vesicles and the cytoplasm, respectively). Interpolyelectrolyte complexes were formed at various polymer/DNA ratios by standard mixing protocols. Dynamic light scattering (DLS) was used to determine the size distributions of the complexes and the relationships between backbone substitution, cation charge density, side-chain hydrolysis, and interpolyelectrolyte complex particle charge. Zeta-potential analysis may also be used to characterize the polymer/DNA complexes. Bronich, T. K.; Nguyen, H. K.; Eisenberg, A.; Kabanov, A. V. (2000) Recognition of DNA Topology in Reactions Between Plasmid DNA and Cationic Polymers. J. Am. Chem. Soc., 122, 8339-8343; Putnam, D.; Gentry, C. A.; Pack, D. W.; Langer, R. (2001) Polymer-Based Gene Delivery with Low Cytotoxicity by a Unique Balance of Side-Chain Termini. Proc. Natl. Acad. Sci. USA, 98, 1200-1205; Lynn, D. M.; Langer, R. (2000) Degradable Poly(β-Amino Esters): Synthesis, Characterization, and Self-Assembly with Plasmid DNA J. Am. Chem. Soc., 122, 10761-10768; Gonzalez, H.; Hwang, S. J.; Davis, M. E. (1999) New Class of Polymers for the Delivery of Macromolecular Therapeutics. Bioconjugate Chem., 10, 1068-1074.

The present polymers have been rationally designed to promote the intracellular dissociation of DNA from interpolyelectrolyte complexes. The functional polymers may change charge states as a function of time, allowing the initial formation of polymer DNA complexes (to address early barriers to transfection) and facilitating intracellular dissociation through the introduction of repulsive electrostatic interactions (to address late barriers). An appropriate balance of charge density and side-chain hydrolysis allows these competing factors to be addressed on a time scale relevant to biological anion delivery/gene transfer and expression. The present polymers may also be designed to have a desired rate of hydrolysis so that the charge shift of the polymer occurs on the desired time scale.

The polymers may be used in the pharmaceutical/drug delivery arts to deliver polynucleotides, proteins, small molecules, peptides, antigen, drugs, or the like to a patient, tissue, organ, cell, or the like.

The polymers may also be used to complex polynucleotides and thereby enhance the delivery of polynucleotide and prevent their degradation. The polymers may also be used in the formation of nanoparticles or microparticles containing encapsulated agents. Due to some of the polymers' properties of being biocompatible and biodegradable, these formed particles are also biodegradable and biocompatible and may be used to provide controlled, sustained release of the encapsulated agent. These particles may also be responsive to pH changes.

Polymers

The present polymers are dynamic charge state cationic polymers that have a cationic charge density which is a characteristic of the polymeric backbone and the functional groups attached to the polymeric backbone. The polymers are designed such that the cationic charge density of the dynamic charge state cationic polymer decreases when one or more of the removable functional group(s) is removed from the dynamic charge state cationic polymer.

Based on these criteria, the polymer backbone is not particularly limited. In some embodiments, the polymer backbone is positively charged, whereas in others the polymeric backbone is neutral. Generally speaking, the charge of the polymer backbone is measured under physiological conditions, such as at physiological pH. In some instances the polymer backbone is made up of repeating units of polyamines, such as polyethyleneimine, polylysine, polyomithine or poly/lysine/ornithine, because such polymers provide the desired cationic charge density and are easy to manipulate. Specific examples of such suitable polymeric backbones include poly(propylene imine), poly(allyl amine), poly(vinyl amine), poly(amidoamine) (PAMAM), and dendrimers that are functionalized with terminal amine groups. Further examples of polymeric backbones suitable for use in the present invention include acrylate or methacrylate polymers such as poly(2-aminoethyl methacrylate), and the like. In some embodiments, where amine functional groups are present in the polymer, primary amines may be functionalized either once or twice to provide a polymer that has a net negative charge once removal of the one or more removable functional group(s) is complete. In the present polymers, the polymeric backbone may be linear, branched or hyperbranched.

The present polymer is generally cationic, but different functional groups attached to the polymer can render the polymer zwitterionic. The present polymer may also be capable of buffering changes in pH which results from the make-up of the polymer backbone and/or the attached functional groups.

Similar to the backbone, the identity of the one or more removable functional group(s) of the present polymers is not particularly limited as long as removal of the one or more removable functional group(s) decreases the cationic charge density of the polymer. As used herein, "removable functional group" means a chemical group that, upon removal, will decrease the cationic charge density of the polymer. As will be apparent to the skilled artisan, polymers whose cationic charge density decreases in this manner can have a variety of features. For example, the removable functional group may be positively charged so that removal of the removable functional group reduces cationic charge density. This may be particularly important where the polymeric backbone is not positively charged. In other embodiments the removable functional group may be positively charged or neutral prior to removal, but provide a negatively charged species after it is removed from the polymer. One example of such a scheme is provided when the removable group contains a hydrolyzable ester. Other configurations that achieve the charge shifting properties of the present polymers will be apparent to those skilled in the art. When removable functional groups provide a negatively charged species after removal from the polymer backbone and the backbone itself is neutral, then the present polymers can shift from being cationic to anionic when the removable functional group is removed.

Examples of removable functional groups suitable for use in the present polymers include side chains that have primary, secondary or tertiary amines. Primary amines useful in the present polymers include, but are not limited to, methylamine, ethylamine, isopropylamine, aniline, substituted anilines, and ethanolamine. In some embodiments, at least one of the one or more removable functional group(s) is a hydrolyzable group, such as a pendant ester. Specific examples for the one or more removable functional group(s)

may also include a labile linkage, such as an ester, an anhydride, an orthoester, a phosphoester, an acetal, or an amide.

The present polymer is generally cationic, but different functional groups attached to the polymer may render the polymer zwitterionic. The present polymer may, also be capable of buffering changes in pH which results from the make-up of the polymer backbone and/or the attached functional groups.

More specifically, polymers having the following structure are suitable for use in the present invention:

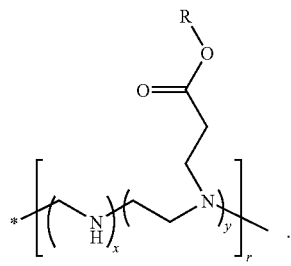

When the polymer has the above formula, n is an integer ranging from 5 to 100,000, x is an integer, and the mole percent of y may range from 10 percent to 100 percent (based on the total of x and y). In the present compounds, the identity of R is not particularly limited. For example, R can be an alkyl, alkenyl, alkynyl, cycloalkyl, heterocyclic, aryl, or heteroaryl group. R may also be carbon-containing, heteroatom containing (N, S, O, P, etc), linear, branched, an amino, an alkylamino, a dialkylamino, a trialkylamino, an aryl, a heterocyclic, a cyano, an amide, a carbamoyl group, or the like. When the R group is alkyl, R can be methyl, ethyl, propyl, butyl, pentyl, hexyl or combinations thereof.

Other examples of polymers include:

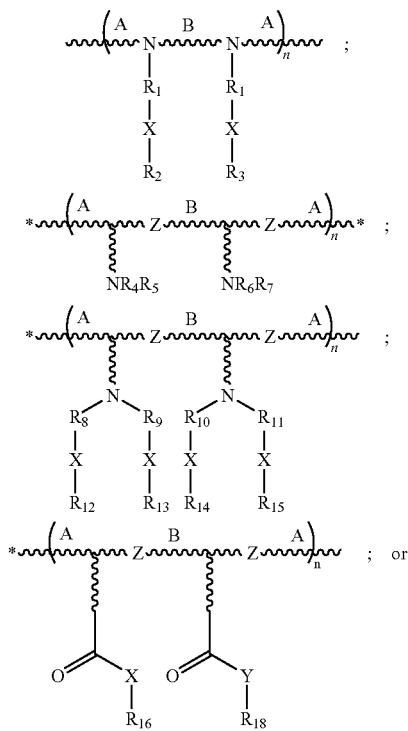

-continued

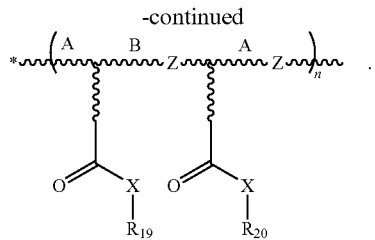

In the above polymers, n is an integer ranging from 5 to 100,000, A and B are linkers which may be the same or different and may be any substituted or unsubstituted, branched or unbranched chain of carbon atoms or heteroatoms; $R_1$ is a linker group or a covalent bond; X is the same or different and is a labile linkage, which, in some instances, is negatively charged after cleavage; Y is a linkage that is generally not as labile as X; $R_2$ through $R_7$ and $R_{12}$ through $R_{20}$ have the value for R listed above and are the same or different; $R_8$, $R_9$, $R_{10}$ and $R_{11}$ are linkers or covalent bonds; and Z is a covalent bond or a degradable linkage. In some embodiments, X is an ester linkage and Y is an amide linkage, such as $NR_{17}$. In some embodiments, $R_{16}$ is $NR_{21}R_{22}$, $R_{17}$ is H, and $R_{18}$ is $NR_{23}R_{24}$. In some embodiments, $R_{19}$ is $NR_{25}R_{26}$, and $R_{20}$ is $NR_{27}R_{28}$. $R_{21}$ through $R_{28}$ may have the value for R listed above and are the same or different. When Z is a covalent bond, the polymer backbone is non-degradable. The linkers A and B may be linkers that include carbon atoms or heteroatoms (e.g., nitrogen, oxygen, sulfur, etc.). Typically, such linkers are 1 to 30 atoms long, or in some case are 1 to 15 atoms long. The linkers may be substituted with various substituents including, but not limited to, hydrogen atoms, and alkyl, alkenyl, alkynyl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, and ureido groups. As would be appreciated by one of skill in the art, each of these groups may in turn be substituted. For some polymers, the ester bond will generally be readily hydrolyzable whereas the amide bond is not readily hydrolyzable. This configuration allows more control over the change of cationic charge density of the polymer by altering the ratio of ester bonds and amide bonds present in the removable functional group(s).

In the present polymers, the mole percent of the monomers comprising the polymeric backbone substituted with the one or more removable functional group(s) range from about 10 percent to about 100 percent or from 10 percent to 100 percent. In additional embodiments, the mole percent of the monomers attached to the one or more removable functional group may range from about 30 percent to 100 percent, from 50 percent to 100 percent, or from 70 percent to 100 percent. The polymers of the present invention may have any desired molecular weight, such as from 1,000 to 100,000 grams/mole, or from about 2,000 to 50,000 grams/mole in some embodiments.

The present dynamic charge state cationic polymers can be non-immunogenic, non-toxic or both non-immunogenic and non-toxic. In the present polymers, polymeric backbone can be degradable or nondegradable. In some embodiments, the polymers of the invention are biodegradable and biocompatible.

The molecular weights of the polymers may range from 5,000 g/mol to over 100,000 g/mol in some embodiments and from 4,000 g/mol to 50,000 g/mol in other embodiments. In some embodiments, the polymers are relatively non-cytotoxic. In other embodiments, the polymers are biocompatible and biodegradable. In one embodiment, the polymers of the present invention have $pK_a$s ranging from 5.5 to 7.5 or, in some embodiments, from 6.0 and 7.0. In other embodiments, the polymer may be designed to have a desired $pK_a$ ranging from 3.0 to 9.0, and in some embodiments from 5.0 to 8.0. The polymers are particularly attractive for drug delivery for several reasons including the following: 1) they may contain amino groups for interacting with DNA and other negatively charged agents, for buffering the pH, for causing endosomolysis, etc.; 2) they may contain degradable polyester linkages; 3) they may be synthesized from commercially available starting materials; and 4) they may be pH responsive and engineered to have a desired $pK_a$.

As described herein, any chemical group that satisfies the valency of each atom may be substituted for any hydrogen atom.

Synthesis of Polymers

The polymers may be prepared by any method known in the art. In some embodiments, the polymers are prepared from commercially available starting materials. In other embodiments, the polymers are prepared from easily and/or inexpensively prepared starting materials.

In some embodiments, the polymer is prepared via conjugate addition of methyl acrylate to linear poly(ethylene imine). Examples of this synthetic scheme are shown in the examples.

The synthesized polymer may be purified by any technique known in the art including, but not limited to, precipitation, crystallization, chromatography, etc. In some embodiments, the polymer need not be purified. In some embodiments, the polymer is purified through repeated precipitations from an organic solvent (e.g., diethyl ether, hexane, etc.). In some embodiments, the polymer is isolated as a salt, such as a hydrochloride salt or a pharmaceutically acceptable salt. As would be appreciated by one of skill in this art, the molecular weight of the synthesized polymer and the extent of cross-linking may be determined by the reaction conditions (e.g., temperature, starting materials, concentration, order of addition, solvent, etc.) used in the synthesis (Odian Principles of Polymerization 3rd Ed., New York: John Wiley & Sons, 1991; Stevens Polymer Chemistry: An Introduction 2nd Ed., New York: Oxford University Press, 1990; each of which is incorporated herein by reference).

In one embodiment, a library of different polymers is prepared in parallel. A different amount of the one or more removable functional group is added to each vial in a set of vials used to prepare the library. The array of vials is incubated at a temperature and length of time sufficient to allow functionalization of the polymers to occur. The polymers may then be isolated and purified using techniques known in the art. The polymers may then be screened using high-throughput techniques to identify polymers with a desired characteristic (e.g., solubility in water, solubility at different pH, ability to bind polynucleotides, ability to bind heparin, ability to bind small molecules, ability to form microparticles, ability to increase transfection efficiency, etc.). In certain embodiments, the polymers may be screened for properties or characteristics useful in gene therapy (e.g., ability to bind polynucleotides, increase in transfection efficiency). In other embodiments, the polymers may be screened for properties or characteristics useful in the art of tissue engineering (e.g., ability to support tissue or cell growth, ability to promote cell attachment).

Interpolyelectrolyte Complexes

The present invention also provides the present polymers complexed with one or more anions thereby forming an interpolyelectrolyte complex. In the interpolyelectrolyte complexes of the present invention, the anion bound by the polymer is not particularly limited. In some embodiments, the anion need only have at least two negative charges. Suitable examples of anionic molecules include nucleic acids, proteins, peptides, carbohydrates, therapeutic molecules or agents, diagnostic molecules or agents, prophylactic agents, small molecules, organometallic compounds, drugs, vaccines, immunological agents, and the like. The anions may be naturally occurring or synthetic as synthetic polyanions may also be used to form interpolyelectrolyte complexes of the invention. In some embodiments, the polymers of the invention are complexed to an anion molecule such as nucleic acids, such as DNA, RNA, or analogs or fragments thereof. In some such embodiments, the polymers may further be complexed to a synthetic polyanion.

The present invention also provides arrays of interpolyelectrolyte complexes arranged on a suitable surface. The arrays can have interpolyelectrolyte complexes that include different combinations of polymers and/or anions at discrete and defined positions. The interpolyelectrolyte arrays can be used for a variety of high-throughput testing procedures, such as drug discovery, cell transfection, and the like. In these methods, cells will be placed, plated and/or cultured on the interpolyelectrolyte array and analyzed. Suitable examples of array configurations and methods for producing and using the present interpolyelectrolyte complex arrays are discussed in U.S. Pat. No. 6,544,790 which is incorporated herein by reference in its entirety and for all purposes as if fully set forth herein.

Polynucleotide Complexes

The ability of cationic compounds to interact with negatively charged polynucleotides through electrostatic interactions is well known. Cationic polymers such as poly(lysine) have been prepared and studied for their ability to complex polynucleotides. The interaction of the polymer with the polynucleotide is thought to at least partially prevent the degradation of the polynucleotide. By neutralizing the charge on the backbone of the polynucleotide, the neutral or slightly-positively-charged complex is also able to more easily enter the cell, for example by traversing through the hydrophobic membranes (e.g., cytoplasmic, lysosomal, endosomal, nuclear) of the cell. In some embodiments, the complex is positively charged. In some embodiments, the complex has a positive zeta-potential, more preferably the zeta-potential is between +1 and +30.

Polynucleotides or derivatives thereof are contacted with the polymers under conditions suitable to form polynucleotide/polymer complexes. The polymer is preferably at least partially protonated so as to form a complex with the negatively charged polynucleotide. In some embodiments, the polynucleotide/polymer complexes form nanoparticles that are useful in the delivery of polynucleotides to cells. In some such embodiments, the diameter of the nanoparticles ranges from 50-500 nm, more preferably the diameter of the nanoparticles ranges from 50-200 nm, and most preferably from 90-150 nm. The nanoparticles may be associated with a targeting agent as described below.

Polynucleotide

The polynucleotide to be complexed or encapsulated by the polymers may be any nucleic acid including but not limited to RNA and DNA. The polynucleotides may be of any size or sequence, and they may be single- or double-stranded. In certain embodiments, the polynucleotide is greater than 100 base pairs long. In certain other embodiments, the polynucleotide is greater than 1000 base pairs long and may be greater than 10,000 base pairs long. The polynucleotide is preferably purified and/or substantially pure. Preferably, the polynucleotide is greater than 50% pure, more preferably greater than 75% pure, and most preferably greater than 95% pure. The polynucleotide may be provided by any means known in the art. In certain embodiments, the polynucleotide has been engineered using recombinant techniques (for a more detailed description of these techniques, please see Ausubel et al. Current Protocols in Molecular Biology (John Wiley & Sons, Inc., New York, 1999); Molecular Cloning: A Laboratory Manual, 2nd Ed., ed. by Sambrook, Fritsch, and Maniatis (Cold Spring Harbor Laboratory Press: 1989); each of which is incorporated herein by reference in its entirety and for all purposes as if fully set forth herein). The polynucleotide may also be obtained from natural sources and purified from contaminating components found normally in nature. The polynucleotide may also be chemically synthesized in a laboratory. In some embodiments, the polynucleotide is synthesized using standard solid phase chemistry.

The polynucleotide may be modified by chemical or biological means. In certain embodiments, these modifications lead to increased stability of the polynucleotide. Modifications include methylation, phosphorylation, end-capping, and the like.

Derivatives of polynucleotides may also be used in the present invention. These derivatives include modifications in the bases, sugars, and/or phosphate linkages of the polynucleotide. Modified bases include, but are not limited to, those found in the following nucleoside analogs: 2-aminoadenosine, 2-thiothymidine, inosine, pyrrolo-pyrimidine, 3-methyl adenosine, 5-methylcytidine, $C^5$-bromouridine, $C^5$-fluorouridine, $C^5$-iodouridine, $C^5$-propynyluridine, $C^5$-propynyl-cytidine, $C^5$-methylcytidine, 7-deazaadenosine, 7-deazaguanosine, 8-oxoadenosine, 8-oxoguanosine, O(6)-methylguanine, and 2-thiocytidine. Modified sugars include, but are not limited to, 2'-fluororibose, ribose, 2'-deoxyribose, 3'-azido-2',3'-dideoxyribose, 2',3'-dideoxyribose, arabinose (the 2'-epimer of ribose), acyclic sugars, and hexoses. The nucleosides may be strung together by linkages other than the phosphodiester linkage found in naturally occurring DNA and RNA. Modified linkages include, but are not limited to, phosphorothioate and 5'-N-phosphoramidite linkages. Combinations of the various modifications may be used in a single polynucleotide. These modified polynucleotides may be provided by any means known in the art. However, as will be appreciated by those of skill in this art, the modified polynucleotides are preferably prepared using synthetic chemistry in vitro.

The polynucleotides to be delivered may be in any form. For example, the polynucleotide may be a circular plasmid, a linearized plasmid, a cosmid, a viral genome, a modified viral genome, an artificial chromosome, or the like.

The polynucleotide may be of any sequence. In certain embodiments, the polynucleotide encodes a protein or peptide. The encoded proteins may be enzymes, structural proteins, receptors, soluble receptors, ion channels, pharmaceutically active proteins, cytokines, interleukins, antibodies, antibody fragments, antigens, coagulation factors, albumin, growth factors, hormones, insulin, etc. The polynucleotide may also comprise regulatory regions to control the expression of a gene. These regulatory regions may include, but are not limited to, promoters, enhancer elements, repressor elements, TATA box, ribosomal binding sites, stop site for transcription, and the like. In other embodiments, the polynucleotide is not intended to encode a protein. For example, the polynucleotide may be used to fix an error in the genome of the cell being transfected.

The polynucleotide may also be provided as an antisense agent or RNA interference (RNAi) agent (Fire et al. Nature 391:806-811, 1998; incorporated herein by reference in its entirety and for all purposes as if fully set forth herein). Antisense therapy is meant to include, e.g., administration or in situ provision of single- or double-stranded oligonucleotides or their derivatives which specifically hybridize, e.g., bind, under cellular conditions, with cellular mRNA and/or genomic DNA, or mutants thereof, so as to inhibit expression of the encoded protein, e.g., by inhibiting transcription and/or translation (Crooke "Molecular Mechanisms of Action of Antisense Drugs" Biochim. Biophys. Acta 1489(1):31-44, 1999; Crooke "Evaluating the Mechanism of Action of Antiproliferative Antisense Drugs" Antisense Nucleic Acid Drug Dev. 10(2):123-126, discussion 127, 2000; Methods in Enzymology volumes 313-314, 1999; each of which is incorporated herein by reference in its entirety and for all purposes as if fully set forth herein). The binding may be by conventional base pair complementarity, or, for example, in the case of binding to DNA duplexes, through specific interactions in the major groove of the double helix (i.e., triple helix formation) (Chan et al. J. Mol. Med. 75(4):267-282, 1997; incorporated herein by reference).

In certain embodiments, the polynucleotide to be delivered comprises a sequence encoding an antigenic peptide or protein. Nanoparticles containing these polynucleotides may be delivered to an individual to induce an immunologic response sufficient to decrease the chance of a subsequent infection and/or lessen the symptoms associated with such an infection. The polynucleotide of these vaccines may be combined with interleukins, interferon, cytokines, and adjuvants such as cholera toxin, KLH, alum, Freund's adjuvant, or the like. A large number of adjuvant compounds are known. A useful compendium of many such compounds is prepared by the National Institutes of Health and can be found on the World Wide Web (http:/www.niaid.nih.gov/daids/vaccine/pdf/compendium.pdf, incorporated herein by reference; see also Allison Dev. Biol. Stand. 92:3-11, 1998; Unkeless et al. Annu. Rev. Immunol. 6:251-281, 1998; and Phillips et al. Vaccine 10:151-158,1992, each of which is incorporated herein by reference in its entirety and for all purposes as if fully set forth herein).

The antigenic protein or peptides encoded by the polynucleotide may be derived from such bacterial organisms as *Streptococccus pneumoniae, Haemophilus influenzae, Staphylococcus aureus, Streptococcus pyogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; from such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; and from such fungal, protozoan, and parasitic organisms such as *Cryptococcus neoformans, Histoplasma*

*capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like.

Microparticles

The polymers of the present invention may also be used to form drug delivery devices. The polymers may be used to encapsulate anionic compounds including polynucleotides, small molecules, proteins, peptides, metals, organometallic compounds, and the like. Some of the present polymers possess one or more property that make them particularly suitable in the preparation of drug delivery devices. Such properties may include 1) the ability of the polymer to complex and protect labile agents; 2) the ability to buffer the pH in the endosome; 3) the ability to act as a "proton sponge" and cause endosomolysis; and 4) the ability to neutralize the charge on negatively charged agents. In some embodiments, the polymers are used to form microparticles containing the agent to be delivered. In some such embodiments, the diameter of the microparticles ranges from 500 nm to 50 micrometers, from 1 micrometer to 20 micrometers, or from 1 micrometer to 10 micrometers. In other embodiments, the microparticles range from 1-5 micrometers. The encapsulating polymer may be combined with other polymers (e.g., PEG, PLGA) to form the microspheres.

Methods of Preparing Microparticles

The microparticles may be prepared using various methods. Examples of such methods include, but are not limited to, spray drying, single and double emulsion solvent evaporation, solvent extraction, phase separation, simple and complex coacervation, and other methods well known to those of ordinary skill in the art. In some embodiments, the methods for preparing the particles are the double emulsion process and spray drying methods. The conditions used in preparing the microparticles may be altered to yield particles of a desired size or property (e.g., hydrophobicity, hydrophilicity, external morphology, "stickiness", shape, etc.). The method of preparing the particle and the conditions (e.g., solvent, temperature, concentration, air flow rate, etc.) used may also depend on the agent being encapsulated and/or the composition of the polymer matrix.

Methods developed for making microparticles for delivery of encapsulated agents are described in the literature (for example, please see Doubrow, M., Ed., "Microcapsules and Nanoparticles in Medicine and Pharmacy," CRC Press, Boca Raton, 1992; Mathiowitz and Langer, J. Controlled Release 5:13-22, 1987; Mathiowitz et al. Reactive Polymers 6:275-283, 1987; Mathiowitz et al. J. Appl. Polymer Sci. 35:755-774, 1988; each of which is incorporated herein by reference).

If the particles prepared by any of the above methods have a size range outside of the desired range, the particles can be sized, for example, using a sieve.

The present polymers and anions may also be combined together to form layered interpolyelectrolyte complexes, similar to those disclosed in Vazquez et al., J. Am. Chem. Soc. 124, 13992 (2002). Such layered interpolyelectrolyte complexes can also be produced by the methods disclosed in Vazquez et al., supra. The number of layers in such an interpolyelectrolyte complex is not particularly limited. Additionally, different layers of these interpolyelectrolyte complexes can contain different polymers and/or anions. The present invention contemplates that these multilayer structures can be used for controlled release of a desired agent or delivery of multiple agents. As is understood by the skilled artisan, the film growth of the layered structure is primarily dictated by electrostatic interactions, hydrophobic interactions, hydrogen bonding, salt concentration, and solution pH. The present layered interpolyelectrolyte complexes can also be used to deliver anions to or transfect cells. In this embodiment the cells to be transfected can be placed or plated on the layered interpolyelectrolyte complexes.

Agent

The agents to be delivered by the system of the present invention may be therapeutic, diagnostic, or prophylactic agents. Any anionic chemical compound to be administered to an individual may be delivered using the interpolyelectrolyte complex. The agent may be a small molecule, organometallic compound, nucleic acid, protein, peptide, polynucleotide, metal, an isotopically labeled chemical compound, drug, vaccine, immunological agent, or the like.

In some embodiments, the agents are organic compounds with pharmaceutical activity. In another embodiment of the invention, the agent is a clinically used drug. In some such embodiments, the drug is an antibiotic, anti-viral agent, anesthetic, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, non-steroidal anti-inflammatory agent, nutritional agent, or the like, or combinations thereof.

In some embodiments of the present invention, the agent to be delivered may be a mixture of agents. For example, a local anesthetic may be delivered in combination with an anti-inflammatory agent such as a steroid. Local anesthetics may also be administered with vasoactive agents such as epinephrine. As a further example, an antibiotic may be combined with an inhibitor of the enzyme commonly produced by bacteria to inactivate an antibiotic (e.g., penicillin and clavulanic acid).

Diagnostic agents include gases; metals; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

Prophylactic agents of the invention include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts. Prophylactic agents may be combined with interleukins, interferon, cytokines, and adjuvants such as cholera toxin, alum, Freund's adjuvant, etc. Prophylactic agents include antigens of such bacterial organisms as *Streptococccus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponemapallidum, Leptospirosis interrogans, Bor-*

*relia burgdorferi, Camphylobacter jejuni*, and the like; antigens of such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

Targeting Agents or Ligands

The micro- and nanoparticles of the invention may be modified to include targeting agents since it is often desirable to target a particular cell, collection of cells, or tissue. A variety of targeting agents that direct pharmaceutical compositions to particular cells are known in the art (see, for example, Cotten et al. Methods Enzym. 217:618, 1993; incorporated herein by reference). The targeting agents may be included throughout the particle or may be only on the surface. The targeting agent may be a protein, peptide, carbohydrate, glycoprotein, lipid, small molecule, antibody, antibody fragment, receptor or the like. The targeting agent may be used to target specific cells or tissues or may be used to promote endocytosis or phagocytosis of the particle. Examples of targeting agents include, but are not limited to, antibodies, fragments of antibodies, low-density lipoproteins (LDLs), transferring, asialycoproteins, gp120 envelope protein of the human immunodeficiency virus (HIV), carbohydrates, receptor ligands, sialic acid, and the like. If the targeting agent is included throughout the particle, the targeting agent may be included in the mixture that is used to form the particles. If the targeting agent is only present on the surface, the targeting agent may be associated with (i.e., by covalent, hydrophobic, hydrogen boding, van der Waals, or other interactions) the formed particles using standard chemical techniques.

The amine groups on the branched PEI can also be conjugated either directly to the amine groups or via spacer molecules, with targeting ligands and the like. Preferably, only a portion of the available amine groups are coupled to the ligand or spacer/ligand such that the net charge of the polymer is positive. The target ligands conjugated to the polymer direct the polymer-nucleic acid/drug complex to bind to specific target cells and penetrate into such cells (tumor cells, liver cells, heamatopoietic cells, and the like). The target ligands can also be an intracellular targeting element, enabling the transfer of the nucleic acid/drug to be guided towards certain favored cellular compartments (mitochondria, nucleus, and the like). In certain embodiments, the ligands can be sugar moieties coupled to the amino groups. Such sugar moieties are preferably mono- or oligo-saccharides, such as galactose, glucose, fucose, fructose, lactose, sucrose, mannose, cellobiose, nytrose, triose, dextrose, trehalose, maltose, galactosamine, glucosamine, galacturonic acid, glucuronic acid, and gluconic acid.

The conjugation of an acid derivative of a sugar with the polymer is preferred in some embodiments. In some such embodiments of the present invention, lactobionic acid (4-O-β-D-galactopyranosyl-D-gluconic acid) is coupled to the polymer. The galactosyl unit of lactose provides a convenient targeting molecule for hepatocyte cells because of the high affinity and avidity of the galactose receptor on these cells.

Other types of ligands that may be used include peptides such as antibodies or antibody fragments, cell receptors, growth factor receptors, cytokine receptors, transferrin, epidermal growth factor (EGF), insulin, asialoorosomucoid, mannose-6-phosphate (monocytes), mannose (macrophage, some B cells), Lewis$^x$ and sialyl Lewis$^x$ (endothelial cells), N-acetyllactosamine (T cells), galactose (colon carcinoma cells), and thrombomodulin (mouse lung endothelial cells), fusogenic agents such as polymixin B and hemaglutinin HA2, lysosomotrophic agents, nucleus localization signals (NLS) such as T-antigen, and the like.

Pharmaceutical Compositions

Once the microparticles or nanoparticles (interpolyelectrolyte complex, e.g. polymer complexed with anionic molecule or compound) have been prepared, they may be combined with one or more pharmaceutical excipients to form a pharmaceutical composition that is suitable to administer to animals. Animals include humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). An animal may be a transgenic animal. As would be appreciated by one of skill in this art, the excipients may be chosen based on the route of administration as described below, the agent being delivered, time course of delivery of the agent, or other factors.

Pharmaceutical compositions of the present invention and for use in accordance with the present invention may include a pharmaceutically acceptable excipient or carrier. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and/or to animals, orally, rectally, parenterally, intracisternally, intravaginally, intranasally, intraperitoneally, topically (as by powders, creams, ointments, or drops), bucally, or as an oral or nasal spray.

Liquid dosage forms for oral administration include pharmaceutically acceptable emulsions, microemulsions, solutions, suspensions, syrups, and elixirs. In addition to the active ingredients (i.e., microparticles, nanoparticles, polynucleotide/polymer complexes), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid may be used in the preparation of injectables. In some embodiments, the particles are suspended in a carrier fluid comprising 1% (w/v) sodium carboxymethyl cellulose and 0.1% (v/v) Tween 80.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the microparticles.

Solid dosage forms for oral administration include capsules, tablets, pills, powders, and granules. In such solid dosage forms, the particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Dosage forms for topical or transdermal administration of an pharmaceutical composition include ointments, pastes, creams, lotions, gels, powders, solutions, sprays, inhalants, or patches. The particles are admixed under sterile conditions with a pharmaceutically acceptable carrier and any needed preservatives or buffers as may be required. Ophthalmic formulation, ear drops, and eye drops are also contemplated as being within the scope of this invention.

The ointments, pastes, creams, and gels may contain, in addition to the particles of this invention, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the particles of this invention, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the microparticles or nanoparticles in a proper medium. Absorption enhancers can also be used to increase the flux of the compound across the skin. The rate can be controlled by either providing a rate controlling membrane or by dispersing the particles in a polymer matrix or gel.

The present invention also provides methods of administering the present polymers and complexes. Generally, these methods can involve contacting an interpolyelectrolyte complex of the present invention with one or more cells, such as those that make up a tissue. In one embodiment, the interpolyelectrolyte complex is administered to an animal. The interpolyelectrolyte complex can be administered in any suitable manner, such as in the manner and formulations described above. In some embodiments, in solution the side chain esters slowly hydrolyze, resulting in the release of the anionic component that is bound electrostatically to the polymer. Some of the present methods can be used to transfect cells.

The present invention also provides methods for delivering an anionic compound to a cell or tissue. The present methods involve contacting a composition that includes a present interpolyelectrolyte complex with a target cell thereby allowing the target cell to uptake the composition. The polymer of the present invention is designed such that when the interpolyelectrolyte complex enters the target cell, one or more of the removable functional group(s) is removed from the dynamic charge state cationic polymer which decreases the cationic charge density of the dynamic charge state cationic polymer. The decrease in the cationic charge density of the polymer is caused by the introduction of anionic charges which promotes dissociation of the interpolyelectrolyte complex into the dynamic charge state cationic polymer and the anionic molecule allowing for delivery of the anionic molecule to the target cell or cell compartment, such as an endosome, cytosol or nucleus of the cell. In some methods, at least one of the one or more of the removable functional group(s) is removed from the dynamic charge state cationic polymer in a nucleus, endosome or cytosol of the target cell. In this manner, the interpolyelectrolyte complex can dissociate primarily in the desired compartment of the target cell and deliver the anionic molecule to the target cell compartment. The present methods can also involve providing the interpolyelectrolyte complex and/or preparing the interpolyelectrolyte complex. Generally, the interpolyelectrolyte complex will be prepared by mixing the dynamic charge state cationic polymer with the anionic molecule thereby allowing formation of the interpolyelectrolyte complex. In the methods where the anionic molecule is DNA, the DNA can be delivered to the nucleus of the cell so that it is stably incorporated into the genome of the target cell. In other embodiments, the DNA is not stably incorporated into the genome of the target cell.

In the present methods, the target cell or tissue can be in vitro or in vivo. Where the target cell or tissue is in vivo, the interpolyelectrolyte complex can be administered to a mammal. In some embodiments of the present methods, the cell is a eukaryotic cell.

In the present methods and polymers, removal of the one or more of the removable functional group(s) from the dynamic charge state cationic polymer can be at least partially hydrolytic, partially enzymatic and/or partially photolytic removal. The present polymers and methods can also be designed so that removal of the one or more of the removable functional groups from the dynamic charge state cationic polymer occurs at a substantially constant rate or does not occur at a constant rate. Accordingly, in the present methods, the majority, or substantially all, of the anions can be delivered to the desired part of the cell, such as the nucleus, endosome or cytosol.

The present invention also provides kits for carrying out the methods described herein. In one embodiment, the kit is made up of instructions for carrying out any of the methods described herein. The instructions can be provided in any intelligible form through a tangible medium, such as printed on paper, computer readable media, or the like. The present kits can also include one or more reagents, buffers, media, nucleic acids, agents and/or disposable equipment in order to readily facilitate implementation of the present methods. Examples of kit components can be found in the description above and in the following examples. Such kits may be used in hospitals, clinics, physician's offices or in patients' homes to facilitate the co-administration of the enhancing and target agents. The kits may also include as an insert printed dosing information for the co-administration of the enhancing and target agents.

These and other aspects of the present invention will be further appreciated upon consideration of the following Examples, which are intended to illustrate certain particular embodiments of the invention but are not intended to limit its scope, as defined by the claims.

Definitions

The following are terms used in the present application:

The term "alkyl" as used herein refers to saturated, straight- or branched-chain hydrocarbon radicals derived from a hydrocarbon moiety containing between one and twenty carbon atoms by removal of a single hydrogen atom. In some embodiments, alkyl groups have from 1 to 12 or from 1 to 8 carbon atoms. Examples of alkyl radicals include, but are not limited to, methyl, ethyl, propyl, isopropyl, n-butyl, tert-butyl, n-pentyl, neopentyl, n-hexyl, n-heptyl, n-octyl, n-decyl, n-undecyl, and dodecyl. A "cycloalkyl" group is a cyclic alkyl group typically containing from 3 to 8 ring members such as, but not limited to, a cyclopropyl, cyclobutyl, cyclopentyl, cyclohexyl, cycloheptyl, or cyclooctyl group.

The term "alkoxy" as used herein refers to an alkyl group, as previously defined, attached to the parent molecular moiety through an oxygen atom. Examples include, but are not limited to, methoxy, ethoxy, propoxy, isopropoxy, n-butoxy, tert-butoxy, neopentoxy, and n-hexoxy groups.

The term "alkenyl" denotes a monovalent group derived from a hydrocarbon moiety having at least one carbon-carbon double bond by the removal of a single hydrogen atom. Alkenyl groups include, for example, ethenyl, propenyl, butenyl, 1-methyl-2-buten-1-yl, and the like.

The term "alkynyl" as used herein refers to a monovalent group derived form a hydrocarbon having at least one carbon-carbon triple bond by the removal of a single hydrogen atom. Representative alkynyl groups include ethynyl, 2-propynyl (propargyl), 1-propynyl, and the like.

The terms "alkylamino", "dialkylamino", and "trialkylamino" as used herein refer to amino groups respectively having one, two, or three alkyl groups, as previously defined, attached to the parent molecular moiety through a nitrogen atom. The term "alkylamino" refers to a group having the structure —NHR' wherein R' is an alkyl group, as previously defined. The term "dialkylamino" refers to a group having the structure —NR'R", where R' and R" are each independently selected from the group consisting of alkyl groups. Finally, the term "trialkylamino" refers to a group having the structure —NR'R"R'", where R', R", and R'" are each independently selected from alkyl groups. Additionally, R', R", and/or R'", taken together, may optionally be a —$(CH_2)_k$— group where k is an integer ranging from 2 to 6. Examples of "alkylamino", "dialkylamino", and "trialkylamino" groups include, but are not limited to, methylamino, dimethylamino, ethylamino, diethylamino, diethylaminocarbonyl, methylethylamino, isopropylamino, piperidino, trimethylamino, and propylamino groups.

The terms "alkylthioether" and "thioalkoxy" refer to an alkyl group, as previously defined, attached to the parent molecular moiety through a sulfur atom.

The term "aryl" as used herein refers to carbocyclic ring systems having at least one aromatic ring including, but not limited to, phenyl, naphthyl, tetrahydronaphthyl, indanyl, and indenyl groups, and the like. Aryl groups can be unsubstituted or substituted with substituents selected from the group consisting of branched and unbranched alkyl, alkenyl, alkynyl, haloalkyl, alkoxy, thioalkoxy, amino, alkylamino, dialkylamino, trialkylamino, acylamino, cyano, hydroxy, halo, mercapto, nitro, carboxyaldehyde, carboxy, alkoxycarbonyl, and carboxamide. In addition, substituted aryl groups include tetrafluorophenyl and pentafluorophenyl.

The terms "heterocyclic" and "heterocyclyl", as used herein, refer to a non-aromatic partially unsaturated or fully saturated 3- to 10-membered ring system, which includes single rings of 3 to 8 atoms in size and bi- and tri-cyclic ring systems which may include aromatic six-membered aryl or aromatic heterocyclic groups fused to a non-aromatic ring. These heterocyclic and heterocyclyl rings and groups include those having from one to three heteroatoms independently selected from oxygen, sulfur, and nitrogen, in which the nitrogen and sulfur heteroatoms may optionally be oxidized and the nitrogen heteroatom may optionally be quaternary.

The terms "aromatic heterocyclic" and "aromatic heterocyclyl", as used herein, refer to a cyclic aromatic radical having from five to ten ring atoms of which one ring atom is selected from sulfur, oxygen, and nitrogen; zero, one, or two ring atoms are additional heteroatoms independently selected from sulfur, oxygen, and nitrogen; and the remaining ring atoms are carbon, the radical being joined to the rest of the molecule via any of the ring atoms. Examples of such aromatic heterocyclyl groups include, but are not limited to, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, and isoquinolinyl groups, and the like.

Specific heterocyclic and aromatic heterocyclic groups that may be included in the compounds of the invention include: 3-methyl-4-(3-methylphenyl)piperazine, 3 methylpiperidine, 4-(bis-(4-fluorophenyl)methyl)piperazine, 4-(diphenylmethyl)piperazine, 4-(ethoxycarbonyl)piperazine, 4-(ethoxycarbonylmethyl)piperazine, 4-(phenylmethyl)piperazine, 4-(1-phenylethyl)piperazine, 4-(1,1-dimethylethoxycarbonyl)piperazine, 4-(2-(bis-(2-propenyl)amino)eth- yl)piperazine, 4-(2-(diethylamino)ethyl) piperazine, 4-(2-chlorophenyl)piperazine, 4-(2-cyanophenyl)piperazine, 4-(2-ethoxyphenyl)piperazine, 4-(2-ethylphenyl)piperazine, 4-(2-fluorophenyl)piperazine, 4-(2-hydroxyethyl)piperazine, 4-(2-methoxyethyl)piperazine, 4-(2-methoxyphenyl)piperazine, 4-(2-methylphenyl)piperazine, 4-(2-methylthiophenyl) piperazine, 4-(2-nitrophenyl)piperazine, 4-(2-nitrophenyl)piperazine, 4-(2-phenylethyl)piperazine, 4-(2-pyridyl)piperazine, 4-(2-pyrimidinyl)piperazine, 4-(2,3-dimethylphenyl)piperazine, 4-(2,4-difluorophenyl) piperazine, 4-(2,4-dimethoxyphenyl) piperazine, 4-(2,4-dimethylphenyl)piperazine, 4-(2,5-dimethylphenyl)piperazine, 4-(2,6-dimethylphenyl)piperazine, 4-(3-chlorophenyl)piperazine, 4-(3-methylphenyl)piperazine, 4-(3-trifluoromethylphenyl)piperazine, 4-(3,4-dichlorophenyl)piperazine, 4-3,4-dimethoxyphenyl)piperazine, 4-(3,4-dimethylphenyl)piperazine, 4-(3,4-methylenedioxyphenyl)piperazine, 4-(3,4,5-trimethoxyphenyl)piperazine, 4-(3,5-dichlorophenyl)piperazine, 4-(3,5-dimethoxyphenyl) piperazine, 4-(4-(phenylmethoxy)phenyl)piperazine, 4-(4-(3,1-dimethylethyl)phenylmethyl)piperazine, 4-(4-chloro-3-trifluoromethylphenyl)piperazine, 4-(4-chlorophenyl)-3-methylpiperazine, 4-(4-chlorophenyl)piperazine, 4-(4-chlorophenyl)piperazine, 4-(4-chlorophenylmethyl) piperazine, 4-(4-fluorophenyl)piperazine, 4-(4-methoxyphenyl)piperazine, 4-(4-methylphenyl)piperazine, 4-(4-nitrophenyl)piperazine, 4-(4-trifluoromethylphenyl) piperazine, 4-cyclohexylpiperazine, 4-ethylpiperazine, 4-hydroxy-4-(4-chlorophenyl)methylpiperidine, 4-hydroxy-4-phenylpiperidine, 4-hydroxypyrrolidine, 4-methylpiperazine, 4-phenylpiperazine, 4-piperidinylpiperazine, 4-(2-furanyl)carbonyl)piperazine, 4-((1,3-dioxolan-5-yl)methyl)piperazine- , 6-fluoro-1,2,3,4-tetrahydro-2-methylquinoline, 1,4-diazacylcloheptane, 2,3-dihydroindolyl, 3,3-dimethylpiperidine, 4,4-ethylenedioxypiperidine, 1,2,3,4-tetrahydroisoquinoline, 1,2,3,4-tetrahydroquinoline, azacyclooctane, decahydroquinoline, piperazine, piperidine, pyrrolidine, thiomorpholine, and triazole.

The term "hydrocarbon", as used herein, refers to any chemical group comprising hydrogen and carbon. The hydrocarbon may be substituted or unsubstituted. The hydrocarbon may be unsaturated, saturated, branched, unbranched, cyclic, polycyclic, or heterocyclic. Illustrative hydrocarbons include, for example, methyl, ethyl, n-propyl, iso-propyl, cyclopropyl, allyl, vinyl, n-butyl, tert-butyl, ethynyl, cyclohexyl, methoxy, diethylamino, and the like. As would be known to one skilled in this art, all valencies must be satisfied in making any substitutions.

The terms "substituted", whether preceded by the term "optionally" or not, and "substituent", as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents may also be further substituted (e.g., an aryl group substituent may be further substituted. For example, a non limiting example is an aryl group that may be further substituted with, for example, a fluorine group at one or more position.

When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, etc.

As used herein, "biodegradable" compounds are those that, when introduced into cells, are broken down by the cellular machinery or by hydrolysis into components that the cells can either reuse or dispose of, in some cases without significant toxic effect on the cells (e.g., fewer than about 20% of the cells are killed when the components are added to cells in vitro). The components preferably do not induce inflammation or other adverse effects in vivo. In certain embodiments, the chemical reactions relied upon to break down the biodegradable compounds are uncatalyzed.

A "labile bond" is a covalent bond that is capable of being selectively broken. That is, a labile bond may be broken in the presence of other covalent bonds without the breakage of other covalent bonds. For example, a disulfide bond is capable of being broken in the presence of thiols without cleavage of any other bonds, such as carbon-carbon, carbon-oxygen, carbon-sulfur, carbon-nitrogen bonds, which may also be present in the molecule. "Labile" also means cleavable.

A "labile linkage" is a chemical compound that contains a labile bond and provides a link or spacer between two other groups. The groups that are linked may be chosen from compounds such as biologically active compounds, membrane active compounds, compounds that inhibit membrane activity, functional reactive groups, monomers, and cell targeting signals. The spacer group may contain chemical moieties chosen from a group that includes alkanes, alkenes, esters, ethers, glycerol, amide, saccharides, polysaccharides, and heteroatoms such as oxygen, sulfur, or nitrogen. The spacer may be electronically neutral, may bear a positive or negative charge, or may bear both positive and negative charges with an overall charge of neutral, positive or negative.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, etc. For example, the effective amount of microparticles containing an antigen to be delivered to immunize an individual is the amount that results in an immune response sufficient to prevent infection with an organism having the administered antigen.

As used herein, "peptide", means peptides of any length and includes proteins. The terms "polypeptide" and "oligopeptide" are used herein without any particular intended size limitation, unless a particular size is otherwise stated. The only limitation to the peptide or protein drug which may be utilized is one of functionality. The terms "protein" and "peptide" may be used interchangeably. Peptide may refer to an individual peptide or a collection of peptides. peptides preferably contain only natural amino acids, although non-natural amino acids (i.e., compounds that do not occur in nature but that can be incorporated into a polypeptide chain; see, for example, http://www.cco.caltech.edu/.about.dadgrp/Unnatstruct.gif, which displays structures of non-natural amino acids that have been successfully incorporated into functional ion channels) and/or amino acid analogs as are known in the art may alternatively be employed. Also, one or more of the amino acids in an peptide may be modified, for example, by the addition of a chemical entity such as a carbohydrate group, a phosphate group, a farnesyl group, an isofarnesyl group, a fatty acid group, a linker for conjugation, functionalization, or other modification, etc. In some embodiments, the modifications of the peptide lead to a more stable peptide (e.g., greater half-life in vivo). These modifications may include cyclization of the peptide, the incorporation of D-amino acids, etc. Typical of peptides that can be utilized are those selected from the group consisting of oxytocin, vasopressin, adrenocorticotrophic hormone, epidermal growth factor, prolactin, luliberin or luteinising hormone releasing hormone, growth hormone, growth hormone releasing factor, insulin, somatostatin, glucagon, interferon, gastrin, tetragastrin, pentagastrin, urogastroine, secretin, calcitonin, enkephalins, angiotensins, renin, bradykinin, bacitracins, polymixins, colistins, tyrocidin, grarnicidines, and synthetic analogues, modifications and pharmacologically active fragments thereof, monoclonal antibodies and soluble vaccines.

The terms "polynucleotide" and "oligonucleotide" refer to a polymer of nucleotides. Typically, a polynucleotide comprises at least three nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, $C^5$-propynylcytidine, $C^5$-propynyluridine, $C^5$-bromouridine, $C^5$-fluorouridine, $C^5$-iodouridine, $C^5$-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds. Known naturally-occurring small molecules include, but are not limited to, penicillin, erythromycin, taxol, cyclosporin, and rapamycin. Known synthetic small molecules include, but are not limited to, ampicillin, methicillin, sulfamethoxazole, and sulfonamides.

As used herein, "administering", and similar terms means delivering the composition to the individual being treated. In some instances the composition is capable of being circulated systemically where the composition binds to a target cell and is taken up by endocytosis. Thus, the composition is preferably administered to the individual systemically, typically by subcutaneous, intramuscular, intravenous, or intraperitoneal administration. Injectables for such use can be prepared in conventional forms, either as a liquid solution or suspension, or in a solid form that is suitable for preparation as a solution or suspension in a liquid prior to injection, or as an emulsion. Suitable excipients include, for example, water, saline, dextrose, glycerol, ethanol, and the like; and if desired, minor amounts of auxiliary substances such as wetting or emulsifying agents, buffers, and the like can be added.

A "pharmaceutically acceptable salt" includes a salt with an inorganic base, organic base, inorganic acid, organic acid, or basic or acidic amino acid. As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, lactic acid, tartaric acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

EXAMPLES

Polymer Synthesis.

The conjugate addition of methyl acrylate to linear polyethylene imine was performed in the following general manner: To a solution of linear polyethylene imine (5 wt % in methanol) was added methyl acrylate (Aldrich). Polyethylene imine was obtained by hydrolyzing polyethyl oxazoline (Polysciences, Warrington, Pa). Typically, the amount of methyl acrylate added was varied (e.g., from 0.25 to 1.2 equivalents relative to amine functionality in the PEI) to achieve desired mole percent substitutions (Table 1). The reaction mixtures were heated to 40° C. and stirred overnight. The resulting products were concentrated by rotary evaporation, dissolved in dichloromethane, and precipitated by hexanes. The precipitate was dried under vacuum to yield the desired product in near quantitative yield. Purified polymers were characterized by nuclear magnetic resonance spectroscopy (NMR), gel permeation chromatography (GPC), and elemental analysis to determine percent functionalization. As a representative example for a polymer with >90% substitution: $^1$H NMR (CDCl$_3$): δ (ppm)=2.45 (t, —CH$_2$CH$_2$N (CH$_2$CH$_2$CO$_2$CH$_3$)); 2.5 (s, —CH$_2$CH$_2$N (CH$_2$CH$_2$CO$_2$CH$_3$)); 2.8 (t, —CH$_2$CH$_2$N (CH$_2$CH$_2$CO$_2$CH$_3$)); 3.7 (s, —CH$_2$CH$_2$N (CH$_2$CH$_2$CO$_2$CH$_3$)). The molecular weights of three sets of functionalized polymers prepared from three different samples of PEI were 8,200 g/mol, 14,000 g/mol, or 34,000 g/mol, as determined by GPC.

| Equivalents of Methyl Acrylate[a] | Percent Polymer Substitution[b] |
|---|---|
| 0.25 eq | 24.8% |
| 0.50 eq | 45.8% |
| 0.75 eq | 79.8% |
| 1.2 eq | 90.9% |

[a]Relative to amine groups in PEI.
[b]Determined by elemental analysis.

In the above table, the percent substitution as determined by elemental analysis is shown for the 14,000 $M_w$ polymer.

Formation of DNA/Polymer Complexes and Agarose Gel Retardation Assays

DNA/polymer complexes were formed by adding 50 μL of a plasmid DNA solution (2 μg/50 μL in water) to a gently vortexing solution of polymer (50 μL in 20 mM HEPES, pH=7.2). In each case, the concentration of polymer in this volume of buffer was adjusted to yield a desired DNA/polymer weight ratio (e.g., 1:1, 1:2, 1:3, etc). These samples were incubated at room temperature for 30 minutes, after which 20 μL of each sample was mixed with a loading buffer and analyzed on a 1% agarose gel (HEPES, 20 mM, pH=7.2, 65V, 30 min). DNA bands were visualized by ethidium bromide staining. Samples used to evaluate time courses of DNA/polymer interaction were prepared as described above and split into 4 equivalent 25 μL samples. These samples were incubated at 37° C. for 0, 24, 48, and 72 hours and analyzed by agarose gel electrophoresis as described above.

Figure 11:
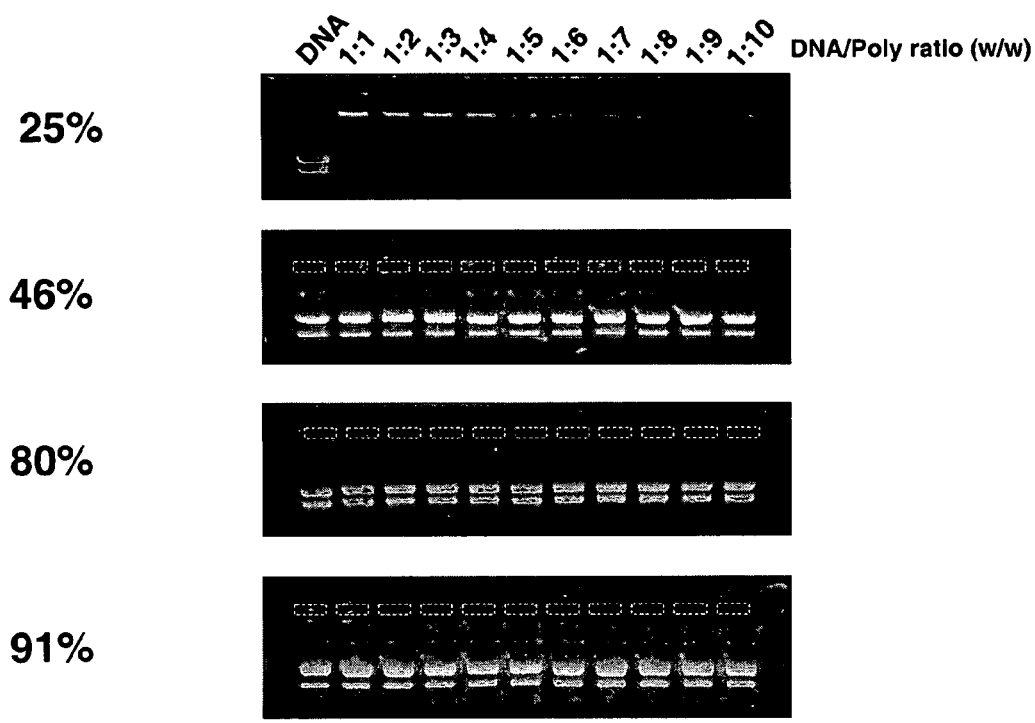

The results of these gel retardation assays are shown in FIGS. 1-11. These figures show the electrophoretic mobility of DNA in the presence of particular polymers of different molecular weights and percent functionalization. As an example, FIG. 1 shows the migration of DNA complexed to PEI 91% substituted with methyl acrylate ($M_w$=14,000 g/mol; polydispersity index (PDI)=2.25 by GPC) as a function of time. The PDI is a measure of how broad the molecular weight distribution is for a given polymer sample. After initial complexation, DNA is bound by polymer and retained in the wells at all weight ratios higher than 1:1 DNA/polymer. At 24 hours, DNA is partially released and at 48 hours, DNA is completely released at all DNA/polymer ratios, as compared to a control experiment employing only DNA. Subsequent Figures show analogous release experiments using polymers of different molecular weights or percent functionalization. It can be seen from the FIGS. that increasing the percent substitution of the polymer results in earlier and more quantitative release of DNA over the range of DNA/polymer ratios and times employed. FIGS. 1-10 demonstrate that varying the molecular weights of these charge dynamic polymers also has a significant influence on the kinetics of DNA release. In these examples, lower molecular weight charge dynamic polymers release DNA more rapidly than higher molecular weight polymers at analogous percent substitutions. NMR suggests that the percent substitution of the polymer used in FIG. 10 was about 50% and not the target 25%. FIG. 11 demonstrates the interaction of completely hydrolyzed samples of the charge dynamic polymers described above with DNA.

Dynamic Light Scattering.

DNA/polymer complexes were formed as described above for agarose gel retardation assays. Samples were diluted with 900 μL of HEPES (20 mM, pH=7.2, total volume=1 mL). Average effective diameters were determined at 25° C. Correlation functions were collected at a scattering angle of 90°, and particle sizes were calculated using the viscosity and refractive index of pure water at 25° C. Particle sizes were calculated and expressed as effective diameters assuming a lognormal distribution.

General Protocol for Cell Transfection Assays.

Transfection assays were performed in triplicate in the following general manner in 96-, 24-, or 6-well cell culture plates. Cells were grown in 96-well plates at initial seeding densities of 15,000 cells/well in 200 μL of growth medium (90% Dulbecco's modified Eagle's medium, 10% fetal bovine serum, penicillin 100 units/mL, streptomycin 100 μg/mL). Cells were grown for 24 hours in an incubator, after which the growth medium was removed and replaced with 200 μL of serum-free or serum-containing medium. DNA/polymer complexes were prepared as described above for gel electrophoresis assays (e.g., using a plasmid containing the firefly luciferase reporter gene (pCMV-Luc)) over the range of different DNA/polymer complexes to be evaluated. An appropriate volume of each sample was added to the cells using a pipette. This volume was typically varied to provide desired concentrations of DNA or DNA/polymer complexes in each well. Controls employing poly(ethylene imine) (PEI) or commercially-available lipid transfection reagents were prepared in a similar manner and included along with DNA and no-DNA controls. Cells were incubated for 4 hours, after which the growth medium was removed and replaced with 200 μL of growth medium. Cells were incubated for an additional period of time (e.g., varied between 24 to 72 hours) and luciferase expression was determined using a commercially available assay kit. Luminescence was quantified in white, solid-bottom polypropylene 96-well plates using a 96-well bioluminescence plate reader. Luminescence was expressed in relative light units, total protein, or light units normalized to total cell protein.

Cytotoxicity Assays.

Cytotoxicity assays were performed in 96-well plates according to the following general protocol: Cells were grown in 96-well plates at initial seeding densities of 10,000 cells/well in 200 μL growth medium (90% Dulbecco's modified Eagle's medium, 10% fetal bovine serum, penicillin 100 units/mL, streptomycin 100 μg/mL). Cells were grown for 24 hours, after which the growth medium was removed and replaced with 180 μL of serum-free medium. Desired amounts of polymer were added in 20 μL aliquots. Samples were incubated at 37° C. for 5 hours, and the metabolic activity of each well was determined using a MTT/thiazolyl blue assay. Generally: to each well was added 25 μL of a 5 mg/mL solution of MTT stock solution in sterile PBS buffer. The samples were incubated at 37° C. for 2 hours, and 100 μL of extraction buffer (20% w/v SDS in DMF/water (1:1), pH=4.7) was added to each well. Samples were incubated at 37° C. for 24 hours. Optical absorbance was measured at 560 nm with a microplate reader and expressed as a percent relative to control cells. This assay was also performed by treating cells with DNA/polymer complexes rather than just dissolved polymer.

The present methods may be carried out by performing any of the steps described herein, either alone or in various combinations. The present compounds may also have any or all of the components described herein. One skilled in the art will recognize that all embodiments of the present invention are capable of use with all other embodiments of the invention described herein. Additionally, one skilled in the art will realize that the present invention also encompasses variations of the present methods and compositions that specifically exclude one or more of the steps, components or groups described herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

All references, patents and publications disclosed herein are specifically incorporated by reference herein in their entireties and for all purposes as if fully set forth herein.

Unless otherwise specified, "a" or "an" means "one or more".

While certain specific embodiments have been illustrated and described, it should be understood that changes and modifications can be made therein in accordance with ordinary skill in the art without departing from the invention in its broader aspects as defined in the following claims.

What is claimed is:

1. An interpolyelectrolyte complex comprising:
   a. a dynamic charge state cationic polymer having a polymeric backbone formed from monomeric units, and one or more removable functional groups attached to the polymeric backbone through one or more labile linkages, wherein the one or more removable functional groups are selected from the group consisting of an alkyl, alkenyl, alkynyl, cycloalkyl, heterocyclic, aryl, and heteroaryl group; and
   b. one or more anions complexed to said cationic polymer; wherein the overall positive charge of the cationic polymer decreases when one or more of the removable functional groups is removed from the polymeric backbone, thereby causing said one or more anions to disassociate from the cationic polymer.

2. The interpolyelectrolyte complex of claim 1, wherein the one or more anions comprises a nucleic acid.

3. The interpolyelectrolyte complex of claim 2, wherein the nucleic acid comprises RNA or DNA.

4. The interpolyelectrolyte complex of claim 2, wherein the nucleic acid encodes a protein or a functional fragment thereof.

5. The interpolyelectrolyte complex of claim 2, wherein the nucleic acid is a plasmid.

6. The interpolyelectrolyte complex of claim 1, wherein the one or more anions comprises a therapeutic molecule, a diagnostic molecule, a peptide, or a carbohydrate.

7. The interpolyelectrolyte complex of claim 6, wherein the carbohydrate is a macromolecular carbohydrate.

8. The interpolyelectrolyte complex of claim 7, wherein the macromolecular carbohydrate is heparin.

9. The interpolyelectrolyte complex of claim 1, wherein the one or more anions comprise a small molecule.

10. The interpolyelectrolyte complex of claim 1, wherein the interpolyelectrolyte complex is from about 50 nm to about 400 nm in size.

11. The interpolyelectrolyte complex of claim 1, comprising one or more layers of the dynamic charge state cationic polymer and one or more layers of the one or more anions.

12. The interpolyelectrolyte complex of claim 1 wherein the one or more removable functional groups are alkyl groups having 1 to 12 carbon atoms.

13. The interpolyelectrolyte complex of claim 1 wherein the one or more removable functional groups are methyl, ethyl, propyl, butyl, pentyl, hexyl groups or combinations thereof.

14. The interpolyelectrolyte complex of claim 1 wherein the polymeric backbone is selected from the group consisting of polyethylene imine, polylysine, polyornithine, poly(propylene imine), poly(allyl amine), poly(vinyl amine), poly(amidoamine), and poly(2-aminoethyl methacrylate).

15. The interpolyelectrolyte complex of claim 1 wherein the polymeric backbone is linear.

16. The interpolyelectrolyte complex of claim 1 wherein the polymeric backbone is linear polyethylene imine.

17. An interpolyelectrolyte complex comprising:
   a. a dynamic charge state cationic polymer having a polymeric backbone formed from monomeric units, and five to 100,000 removable functional groups attached to the polymeric backbone through five to 100,000 labile linkages, wherein the five to 100,000 removable functional groups are selected from the group consisting of an alkyl, alkenyl, alkynyl, cycloalkyl, heterocyclic, aryl, heteroaryl, amino, alkylamino, cyano, amide, and carbamoyl group; and
   b. one or more anions complexed to said cationic polymer; wherein the overall positive charge of the cationic polymer decreases when any of the five to 100,000 of the removable functional groups is removed from the polymeric backbone, thereby causing said one or more anions to disassociate from the cationic polymer.

18. The interpolyelectrolyte complex of claim 17 wherein the five to 100,000 removable functional groups are selected from the group consisting of methyl, ethyl, propyl, butyl, pentyl, hexyl groups and combinations thereof.

19. The interpolyelectrolyte complex of claim 17 wherein the polymeric backbone is selected from the group consisting of polyethylene imine, polylysine, polyornithine, poly(propylene imine), poly(allyl amine), poly(vinyl amine), poly(amidoamine), and poly(2-aminoethyl methacrylate).

20. The interpolyelectrolyte complex of claim 17 wherein the polymeric backbone is linear.

21. The interpolyelectrolyte complex of claim 17 wherein the polymeric backbone is linear polyethylene imine.

22. The interpolyelectrolyte complex of claim 17 comprising a dynamic charge state cationic polymer having the formula:

$$*{-}\left[\left(NH\right)_x\left(N\begin{array}{c}\phantom{x}\\\phantom{x}\end{array}\right)_y\right]_r{-}$$

wherein n is an integer ranging from 5 to 100,000, x is an integer, y is an integer, wherein the mole percent of y ranges from 10 percent to 100 percent based on the total amount of x and y, and R is a removable functional group selected from an alkyl, alkenyl, alkynyl, cycloalkyl, heterocyclic, aryl, or heteroaryl group.

23. The interpolyelectrolyte complex of claim 22 wherein R is an alkyl group having 1 to 12 carbon atoms.

24. The interpolyelectrolyte complex of claim 22 wherein R is a methyl, ethyl, propyl, butyl, pentyl, hexyl group or combinations thereof.

25. The interpolyelectrolyte complex of claim 22 wherein the molecular weight of the dynamic charge state cationic polymer ranges from about 1,000 to about 100,000 grams/mole.

26. An interpolyelectrolyte complex comprising:
   a. a dynamic charge state cationic polymer having a polymeric backbone formed from monomeric units, and one or more removable functional groups attached to the polymeric backbone through one or more labile linkages, wherein the mole percent of monomeric units of the polymeric backbone attached to the one or more removable functional groups is between about 10 percent to about 100 percent, wherein the one or more removable functional groups are selected from the group consisting of an alkyl, alkenyl, alkynyl, cycloalkyl, heterocyclic, aryl, heteroaryl, amino, alkylamino, cyano, amide, and carbamoyl group; and
   b. one or more anions complexed to said cationic polymer;
   wherein the overall positive charge of the cationic polymer decreases when one or more of the removable functional groups is removed from the polymeric backbone, thereby causing said one or more anions to disassociate from the cationic polymer.

27. The interpolyelectrolyte complex of claim 26 wherein the mole percent of monomeric units of the polymeric backbone attached to the one or more removable functional groups is between about 30 percent to 100 percent.

28. The interpolyelectrolyte complex of claim 26 wherein the mole percent of monomeric units of the polymeric backbone attached to the one or more removable functional groups is between about 50 percent to 100 percent.

29. The interpolyelectrolyte complex of claim 26 wherein the mole percent of monomeric units of the polymeric backbone attached to the one or more removable functional groups is between about 70 percent to 100 percent.

30. The interpolyelectrolyte complex of claim 26 wherein the one or more removable functional groups are selected from the group consisting of methyl, ethyl, propyl, butyl, pentyl, hexyl groups and combinations thereof.

31. The interpolyelectrolyte complex of claim 26 wherein the polymeric backbone is selected from the group consisting of polyethylene imine, polylysine, polyornithine, poly(propylene imine), poly(allyl amine), poly(vinyl amine), poly(amidoamine), and poly(2-aminoethyl methacrylate).

32. The interpolyelectrolyte complex of claim 26 wherein the polymeric backbone is linear.

33. The interpolyelectrolyte complex of claim 26 wherein the polymeric backbone is linear polyethylene imine.

* * * * *